(12) United States Patent
Morioka

(10) Patent No.: US 9,566,231 B2
(45) Date of Patent: Feb. 14, 2017

(54) AQUEOUS HAIR CLEANSING AGENT

(75) Inventor: Tomoki Morioka, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 32 days.

(21) Appl. No.: 14/235,720

(22) PCT Filed: Jul. 30, 2012

(86) PCT No.: PCT/JP2012/004836
§ 371 (c)(1),
(2), (4) Date: Jan. 28, 2014

(87) PCT Pub. No.: WO2013/014951
PCT Pub. Date: Jan. 31, 2013

(65) Prior Publication Data
US 2014/0166034 A1    Jun. 19, 2014

(30) Foreign Application Priority Data

Jul. 28, 2011  (JP) .................................. 2011-165499

(51) Int. Cl.
*A61K 8/891*  (2006.01)
*A61Q 5/06*   (2006.01)
(Continued)

(52) U.S. Cl.
CPC ............... *A61K 8/891* (2013.01); *A61K 8/463* (2013.01); *A61K 8/731* (2013.01); *A61K 8/737* (2013.01); *A61K 8/8158* (2013.01); *A61K 8/898* (2013.01); *A61Q 5/02* (2013.01); *A61Q 5/06* (2013.01); *A61K 2800/5426* (2013.01)

(58) Field of Classification Search
None
See application file for complete search history.

(56) References Cited

U.S. PATENT DOCUMENTS 5,747,016 A    5/1998  Yui et al.
6,726,902 B1   4/2004  Müller et al.
(Continued)

FOREIGN PATENT DOCUMENTS

DE    296 08 799 U1    9/1997
DE    196 19 661 A1   11/1997
(Continued)

OTHER PUBLICATIONS

Guar Gum. <http://www.guargum.biz/guargum_chemical_structure.html>, available Feb. 2002; accessed Dec. 11, 2015.*
(Continued)

*Primary Examiner* — Ileana Popa
*Assistant Examiner* — Nicole Babson
(74) *Attorney, Agent, or Firm* — Oblon, McClelland, Maier & Neustadt, L.L.P.

(57) ABSTRACT

An aqueous hair cleansing agent containing the following components (A), (B) and (C) and water:
(A) an anionic surfactant;
(B) a specific organo polysiloxane; and
(C) one or more of cationized polymer(s) selected from (c-1) and (c-2):
(c-1) a cationized polymer having cellulose skeleton or galactomannan skeleton; and
(c-2) a cationic polymer having diallyl dimethylammonium salt skeleton.

17 Claims, 1 Drawing Sheet

(51) Int. Cl.
*A61K 8/46* (2006.01)
*A61Q 5/02* (2006.01)
*A61K 8/73* (2006.01)
*A61K 8/81* (2006.01)
*A61K 8/898* (2006.01)

(56) References Cited

U.S. PATENT DOCUMENTS

| | | |
|---|---|---|
| 2004/0170593 A1 | 9/2004 | Müller et al. |
| 2006/0198807 A1 | 9/2006 | Morioka |
| 2006/0223728 A1* | 10/2006 | Tokunaga ............... A61K 8/362 510/124 |
| 2010/0203002 A1 | 8/2010 | Fukuhara et al. |
| 2013/0310295 A1 | 11/2013 | Iwai |

FOREIGN PATENT DOCUMENTS

| | | |
|---|---|---|
| EP | 0 640 643 A2 | 3/1995 |
| JP | 3 287509 | 12/1991 |
| JP | 4 36226 | 2/1992 |
| JP | 5 112423 | 5/1993 |
| JP | 2002 53440 | 2/2002 |
| JP | 2010 138099 | 6/2010 |
| JP | 2011 105660 | 6/2011 |
| JP | 2011 126978 | 6/2011 |
| WO | 2009 014237 | 1/2009 |
| WO | WO 2012/066722 A1 | 5/2012 |

OTHER PUBLICATIONS

International Search Report Issued Oct. 23, 2012 in PCT/JP12/004836 Filed Jul. 30, 2012.
Extended European Search Report issued Apr. 14, 2015 in Patent Application No. 12818008.0.

* cited by examiner

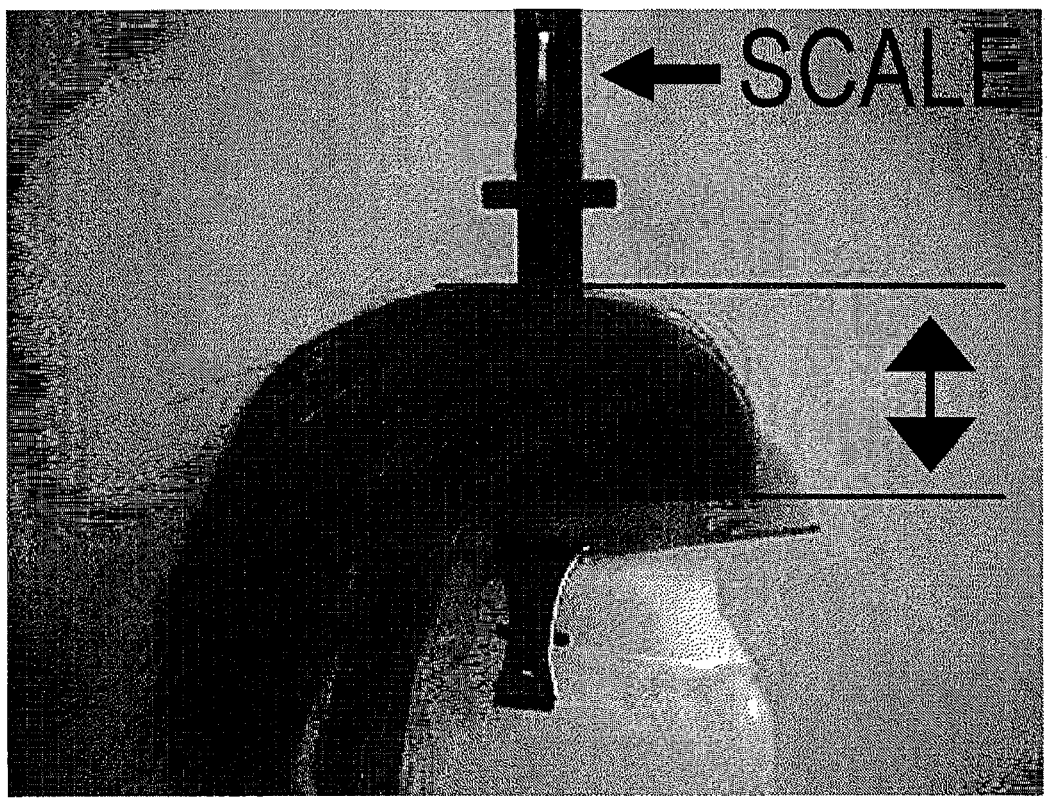

AQUEOUS HAIR CLEANSING AGENT

CROSS REFERENCE TO RELATED APPLICATION

This application is a 371 of PCT/JP2012/004836, filed on Jul. 30, 2012, and claims priority to Japanese Patent Application No. 2011-165499, filed on Jul. 28, 2011.

TECHNICAL FIELD

The present invention relates to an aqueous hair cleansing agent.

BACKGROUND ART

In recent years, function for providing a conditioning effect is critical for hair cleansing agents, in addition to basic functions as the cleansing agent such as foaming, cleansing-ability and the like.

Patent Document 1 describes that a specific amount of a cationic derivative of guar gum is employed in a shampoo composition and an aqueous emulsion of insoluble and involatile silicone containing a specific size of dispersed silicone is employed, in order to improve hair conditioning characteristics of the shampoo composition.

Patent Document 2 describes that a combination of an organic carboxylic acid and a specific organic solvent and a specific organo polysiloxane (modified silicone) is employed to obtain a hair cosmetic composition, which exhibits enhanced manageability and touch feel of the hair and enhanced styling-abilities of both of the set-ability just after coiffed and the style-holding effect.

In addition to above, other technologies employing modified silicones include a technology described in Patent Document 3.

RELATED DOCUMENTS

Patent Documents

[Patent Document 1] Japanese Laid-Open Patent Publication No. H04-36,226 (1992);
[Patent Document 2] Japanese Laid-Open Patent Publication No. 2009-46,466; and
[Patent Document 3] Japanese Laid-Open Patent Publication No. H03-287,509 (1991).

SUMMARY OF THE INVENTION

The present invention relates to an aqueous hair cleansing agent containing the following components (A), (B) and (C) and water:
(A) an anionic surfactant;
(B) an organo polysiloxane, in which a poly(N-acyl alkylene imine) segment composed of repeating units represented by the following general formula (1) is bound to at least two silicon atoms in an organo polysiloxane segment constituting a main chain through alkylene group containing hetero atom,

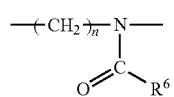

(1)

wherein, in the above-described formula (1), $R^6$ represents a hydrogen atom, or alkyl group, aralkyl group or aryl group of 1 to 22 carbon atom(s), and n represents 2 or 3,
wherein number-average molecular weight of the poly (N-acyl alkylene imine) segment is within a range from $5.0 \times 10^2$ to $1.8 \times 10^3$, the mass ratio (a/b) of the organo polysiloxane segment (a) constituting the main chain to the poly(N-acyl alkylene imine) segment (b) is within a range from 65/35 to 82/18, and weight-average molecular weight of the organo polysiloxane segment constituting the main chain is within a range from $1 \times 10^4$ to $1 \times 10^5$; and
(C) one or more of cationized polymer(s) selected from (c-1) and (c-2):
(c-1) a cationized polymer having cellulose skeleton or galactomannan skeleton; and
(c-2) a cationic polymer having diallyl dimethylammonium salt skeleton.

BRIEF DESCRIPTION OF THE DRAWINGS

FIG. 1 A diagram, which is useful for describing a method for evaluating easiness in causing the rising of the hair.

DESCRIPTION OF EMBODIMENTS

When a component such as a silicone or a cationic polymer is blended in a hair cleansing agent, conditioning effect is improved, and on the other hand, the hair cleansing agent containing the conditioning component is remained on the hair, resulting in the weight of which may weigh the hairstyle down after the drying.

Thus, this may cause troubles for persons, for example, having smaller amount of hair or having thin and fine hair who feels unpleasant stickiness of remained conditioning agent or who cannot obtain voluminous hair due to the weighing-down of the hair style.

The present invention relates to an aqueous hair cleansing agent, which exhibits well-balanced performances in the rising of the hair after shampooing and drying, the volume-up effect and the conditioning characteristic.

The aqueous hair cleansing agent according to the present invention contains the following components (A), (B) and (C) and water:
(A) an anionic surfactant;
(B) an organo polysiloxane, in which a poly(N-acyl alkylene imine) segment composed of repeating units represented by the following general formula (1) is bound to at least two silicon atoms in organo polysiloxane segment constituting main chain through alkylene group containing hetero atom,

(1)

wherein, in the above-described general formula (1), $R^6$ represents hydrogen atom, or alkyl group, aralkyl group or aryl group of 1 to 22 carbon atom(s), and n represents 2 or 3,
wherein the number-average molecular weight of the poly (N-acyl alkylene imine) segment is within a range from $5.0 \times 10^2$ to $1.8 \times 10^3$, the mass ratio (a/b) of the organo polysiloxane segment (a) constituting the main chain to the poly(N-acyl alkylene imine) segment (b) is within a range from 65/35 to 82/18, and the weight-average molecular weight of the organo polysiloxane segment constituting the main chain is within a range from $1 \times 10^4$ to $1 \times 10^5$; and
(C) one or more of cationized polymer(s) selected from (c-1) and (c-2):
(c-1) a cationized polymer having cellulose skeleton or galactomannan skeleton; and
(c-2) a cationic polymer having diallyl dimethylammonium salt skeleton.

According to the present invention, an aqueous hair cleansing agent, which exhibits well-balanced performances in the rising of the hair after shampooing and drying, the volume-up effect and the conditioning characteristic can be obtained.

Each of the components (A) to (C) will be described below, in reference to specific examples. In addition, each of the respective components may be employed alone, or combination of two or more thereof may be employed.
(Component (A))

Specific examples of anionic surfactants for component (A) include: sulfate-type anionic surfactants such as alkyl sulfate, alkenyl sulfate, polyoxyalkylene alkyl ether sulfate, polyoxyalkylene alkenyl ether sulfate, alkylene sulfosuccinate alkyl phenyl ether sulfate and the like; sulfonic acid-type anionic surfactants such as alkyl sulfosuccinate ester salt, polyoxyalkylene alkyl sulfosuccinate ester salt, alkanesulfonate and the like; and carboxylic acid-type anionic surfactants such as higher fatty acid salt, alkyl ether carboxylic acid or a salt thereof and the like. It is preferable to employ one type or two or more types selected from the above-described anionic surfactants. Among these, polyoxyalkylene alkyl ether sulfate, polyoxyalkylene alkenyl ether sulfate, alkyl sulfate and alkenyl sulfate are preferable, and further compounds represented by the following general formula (11) is preferable for polyoxyethylene alkyl ether sulfate.

$$R^{11}O(CH_2CH_2O)_uSO_3M \qquad (11)$$

In the above-described general formula (11), $R^{11}$ represents alkyl group or alkenyl group of 10 to 18 carbon atoms, M represents alkali metal, alkaline earth metal, ammonium, alkanolamine or basic amino acid, and U represents a number of 0.5 to 5 in mass average.

Among these, in view of satisfying both of rapid foaming and good touch of the foam, it is preferable that $R^{11}$ in the general formula (11) is alkyl group of 12 to 14 carbon atoms. Also, average addition molar number of ethylene oxide in the composition is preferably 0.5 to 5, and more preferably 0.9 to 4, and is further preferably 1 to 3. Further, it is preferable to employ polyoxyethylene alkyl ether sulfate, in which M is ammonium or sodium.

The content of the component (A) may be, in view of further enhancing the foaming, preferably equal to or higher than 1% by mass for the whole aqueous hair cleansing agent, and more preferably equal to or higher than 5% by mass, and is further preferably equal to or higher than 8% by mass. Also, in view of improvement in quick to rinse off and residue feel in rinsing, the content of the component (A) in the whole aqueous hair cleansing agent is preferably equal to or lower than 30% by mass, and more preferably equal to or lower than 25% by mass, and is further preferably equal to or lower than 15% by mass.
(Component (B))

The component (B) is an organo polysiloxane, in which a poly(N-acyl alkylene imine) segment composed of repeating units represented by the following general formula (1) is bound to at least two silicon atoms in organo polysiloxane segment constituting main chain through alkylene group containing hetero atom,

wherein, in the above-described general formula (1), $R^6$ represents hydrogen atom, or alkyl group, aralkyl group or aryl group of 1 to 22 carbon atom(s), and n represents 2 or 3,
wherein the number-average molecular weight of the poly (N-acyl alkylene imine) segment is within a range from $5.0 \times 10^2$ to $1.8 \times 10^3$, the mass ratio (a/b) of the organo polysiloxane segment (a) constituting the main chain and the poly(N-acyl alkylene imine) segment (b) is within a range from 65/35 to 82/18, and the weight-average molecular weight of the organo polysiloxane segment constituting the main chain is within a range from $1 \times 10^4$ to $1 \times 10^5$.

Meanwhile, according to the investigations of the present inventors, when the hair cleansing agent containing the conditioning components is remained on the hair, the remained agent leads to weighing the hair down after drying, as described above. On the other hand, when the conditioning component that is considered to be the cause of the weighing-down is merely removed from the hair cleansing agent, the expected effect cannot possibly be sufficiently achieved without maintaining the volumetric hair style by hardening the hair with a hair spray, even reduction of the hair volume is reduced to a certain extent. Also, the smoothness of the hair and the natural finish without the stickiness cannot possibly be achieved after drying without employing the conditioning component.

The present inventors conducted further investigations on the basis of the above-described knowledge in order to achieve both of enhanced volume-up effect and enhanced conditioning effect, and eventually have found that the weighing-down of the hair after drying can be effectively suppressed by employing a polymer of the component (B). Further, it have also found that the volume of the hair after drying can be increased while ensuring sufficient conditioning effect by blending the component (B) in the aqueous hair cleansing agent in combination with the component (C) as will be discussed later together with the above-described component (A).

In addition, the component (B) of the present invention is a polymer, in which the storage elastic modulus, the adhesion and the weight-average molecular weight are within specific ranges. More specifically, it is the polymer having the following characteristics, which are obtainable by measuring the characteristics such as the storage elastic modulus, the adhesion and the like.

The polymer exhibits that: the storage elastic modulus at 20 degrees C. is within a range from $1 \times 10^5$ to $1 \times 10^7$ Pa, which is measured under the condition that the temperature is elevated at a speed of 5 degrees C./2 minutes after the temperature is decreased from 25 degrees C. to −130 degrees C. in 30 minutes at a frequency of 2 Hz and with a strain of 0.01%; the adhesion measured according to JIS-Z 3284 is within a range from 50 to 500 gf; and the weight-average molecular weight thereof is within a range from $5 \times 10^2$ to $5 \times 10^5$.

The storage elastic modulus of the component (B) within the above-described range provides appropriate body or bouncy for the hair after drying, allowing to raise the hair. In the present invention, the storage elastic modulus of the component (B) is the storage elastic modulus at 20 degrees C., which is measured under the condition that the temperature is elevated at a speed of 5 degrees C./2 minutes after the decrease in the temperature from 25 degrees C. to −130 degrees C. is carried out in 30 minutes, and is measured by the following method.

(Measuring Method for Storage Elastic Modulus)

The measurements are carried out in the following procedures by employing a rheometer (for example, "MCR500 Rheometer", commercially available from ANTON PARR Co., Ltd.).

(1) The polymer of the object for the measurement is placed on a lower disc, and a 6 mm-ϕ disc with a trench is set.

(2) The disc is pressed under the following measurement conditions to carry out the measurement.

(Conditions of Measurement for Storage Elastic Modulus)
Rate of Temperature Drop: from room temperature (25 degrees C.) to −130 degrees C./30 min.;
Measurement Frequency: 2 Hz;
Measurement Strain: 0.01%;
Rate of Temperature Elevation: approximately 5 degrees C./2 min.

In view of firmly obtaining volume-up effect for the hair after drying, the storage elastic modulus of the component (B) is equal to or higher than $1 \times 10^5$ Pa, and is preferably equal to or higher than $3 \times 10^5$ Pa, and is further preferably equal to or higher than $5 \times 10^5$ Pa. Also, in view of providing natural hairstyle and stably obtaining the volume-up effect of the hair after drying, the storage elastic modulus of the component (B) is equal to or lower than $1 \times 10^7$ Pa, and is preferably equal to or lower than $8 \times 10^6$ Pa, and further preferably equal to or lower than $6 \times 10^6$ Pa. In addition to above, for example, a polymer, which is in solid or semisolid state at 20 degrees C. may be employed for the component (B).

Also, in view of providing improved handling ability for the hair throughout the shampooing, the rinsing and the drying with the dryer and the like, it is preferable that the component (B) is a thermoplastic polymer.

At this time, the storage elastic modulus of the component (B) at 40 degrees C. is equal to or higher than $5 \times 10^4$ Pa, which is lower than the storage elastic modulus at 20 degrees C., and is preferably within a range from $5 \times 10^4$ to $1 \times 10^6$ Pa.

On the other hand, the storage elastic modulus of the component (B) at 80 degrees C. is equal to or higher than $3 \times 10^4$ Pa, which is lower than the storage elastic modulus at 20 degrees C. and at 40 degrees C., and is preferably within a range from $3 \times 10^4$ to $1 \times 10^5$ Pa.

Also, the adhesion of the component (B) within the above-described range suppresses slippage of hair and control the weight-hair down due to this slippage, so that the hair volume can be maintained.

In the present invention, the adhesion of the component (B) is measured according to JIS Z 3284 (appendix 9), and more specifically by the following method.

(Method for Measuring Adhesion)

A tackiness tester (for example, "TACKINESS TESTER MODEL TAC-II" commercially available from Rhesca Co., Ltd.) is employed to measure the tackiness as follows.

(1) A polymer of the object for the measurement is placed on a glass plate, and is set in a stage of a tackiness tester.

(2) Maximum resistances are measured seven times in 10 minutes, and each of the measurements is carried out when a probe is raised by 2 mm after pushing the probe against a cured product under the following measurement conditions, and the average thereof is determined as tackiness.

(Measurement Conditions for Adhesion)
Plate temperature: room temperature (25 degrees C.) (temperature of sample stage)
Probe temperature: 35 degrees C. (polystyrene plate is adhered on the leading end of the probe (diameter 5 mm).)
Approaching speed: 120 mm/min.
Pre-load: 20 gf (force of pressurizing the probe against the cured product)
Pressing time: 5 seconds (time of pressurizing the probe against the cured product)
Testing rate: 600 mm/min. (speed for raising the probe from the cured product)
Raising distance: 5 mm.

In view of firmly obtaining the volume-up effect for the hair after drying, the adhesion of the component (B) is equal to or higher than 50 gf, and is preferably equal to or higher than 100 gf. On the other hand, in view of stably obtaining the volume-up effect for the hair after drying, the adhesion of the component (B) is equal to or lower than 500 gf, and is preferably equal to or lower than 400 gf.

Also, the weight-average molecular weight of the component (B) is, in view of firmly obtaining the volume-up effect for the hair after drying, equal to or higher than $5 \times 10^2$, and is preferably equal to or higher than $1 \times 10^3$, and is more preferably equal to or higher than $1 \times 10^4$, and even more preferably equal to or higher than $2 \times 10^4$. On the other hand, in view of stably obtaining the volume-up effect for the hair after drying, the weight-average molecular weight of the component (B) is equal to or lower than $5 \times 10^5$, and is preferably equal to or lower than $1 \times 10^5$.

Specific types of organo polysiloxanes are exemplified for the component (B) having the characteristics as described above. More specifically, it is typically an organo polysiloxane, in which a poly(N-acyl alkylene imine) segment composed of repeating units represented by the following general formula (1) is bound to at least two silicon atoms in organo polysiloxane segment constituting main chain through alkylene group containing hetero atom, the number average molecular weight of the poly (N-acyl alkylene imine) segment is within a range from $5.0 \times 10^2$ to $1.8 \times 10^3$, the mass ratio (a/b) of the organo polysiloxane segment (a) constituting the main chain and the poly(N-acyl alkylene imine) segment (b) is within a range from 65/35 to 82/18, and the weight-average molecular weight of the organo polysiloxane segment constituting the main chain is within a range from $1 \times 10^4$ to $1 \times 10^5$. It is preferable to employ one, two or more selected from the above-described specific organo polysiloxanes.

(1)

In the above-described general formula (1), $R^6$ represents a hydrogen atom, or alkyl group, aralkyl group or aryl group of 1 to 22 carbon atom(s), and n represents 2 or 3.

Among elements or groups represented by $R^6$ in the above-described general formula (1), for example, linear, branched or cyclic alkyl groups of 1 to 22 carbon atom(s) are exemplified for the alkyl group of 1 to 22 carbon atom(s), and more specifically, methyl group, ethyl group, n-propyl group, isopropyl group, n-butyl group, tert-butyl group, pentyl group, hexyl group, cyclohexyl group, heptyl group, octyl group, nonyl group, decyl group, undecyl group, dodecyl group, octadecyl group, nonadecyl group, eicosyl group, docosyl group and the like are exemplified. Among these, alkyl group of 1 to 10 carbon atom(s) is preferable, and alkyl group of 1 to 6 carbon atom(s) is more preferable. On the other hand, for example, typical aralkyl group include aralkyl groups of 7 to 19 carbon atoms, and more specifically, benzyl group, phenethyl group, trityl group, naphthylmethyl group, anthracenyl methyl group and the like are exemplified. Among these, aralkyl groups of 7 to 14 carbon atoms are preferable, and aralkyl groups of 7 to 10 carbon atoms are more preferable. Further, typical aryl group include aryl groups of 6 to 14 carbon atoms, and more specifically, phenyl group, tolyl group, xylyl group, naphthyl group, biphenyl group, anthryl group, phenanthryl group and the like are exemplified, and among these, aryl groups of 6 to 12 carbon atoms are preferable, and aryl groups of 6 to 9 carbon atoms are more preferable.

Among these, alkyl groups of 1 to 6 carbon atom(s) are further preferable for $R^6$.

Also, alkylene group containing hetero atom functions as a coupling group for poly (N-acyl alkylimine) segment, and typical alkylene group of such type includes, for example, alkylene groups of 2 to 20 carbon atoms having 1 to 3 of nitrogen atom, oxygen atom or sulfur atom in molecule are exemplified, among these, groups represented by the following formula (i) to (vii) are preferable, and groups represented by the following formula (i) and (ii) are more preferable. In addition to above, in the following formula, An- represents anion, and for example, ethylsulfate ion, methylsulfate ion, chlorine ion, iodine ion, sulfate ion, p-toluenesulfonic acid ion, perchlorate ion are exemplified.

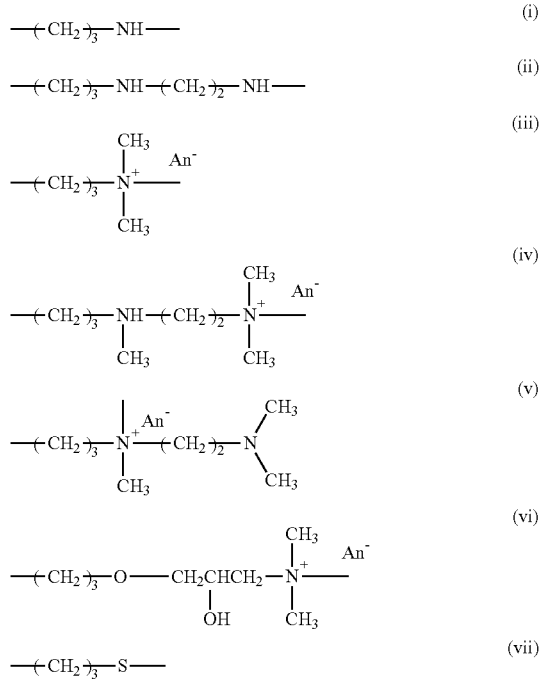

While the mass ratio (a/b) of the organo polysiloxane segment (a) and the poly(N-acyl alkylene imine) segment (b) is within a range from 65/35 to 82/18, it is preferably 68/32 to 80/20 in view of volume and feel of the hair, and is more preferably 70/30 to 79/21.

In addition to above, in the present Specification, the mass ratio (a/b) is a value derived from integration ratio between alkyl group or phenyl group in organo polysiloxane segment and methylene group in poly(N-acylalkylene imine) segment obtained by nuclear magnetic resonance ($^1$H-NMR) analysis, in which 5% by mass of organo polysiloxane of the present invention is dissolved in deuterated chloroform.

The weight-average molecular weight (MWg) of organo polysiloxane segments between adjacent poly(N-acylalkylene imine) segments is preferably $1.5 \times 10^3$ to $3.5 \times 10^3$, and more preferably $1.6 \times 10^3$ to $3.2 \times 10^3$ in view of volume and feel of the hair, and is further preferably $1.7 \times 10^3$ to $3.0 \times 10^3$.

In the present specification, "organo polysiloxane segments between adjacent poly(N-acylalkylene imine) segments" means a section surrounded with dotted line between two bonding sites from bonding site (bonding site α) of poly(N-acylalkylene imine) segment in organo polysiloxane segment to bonding site (bonding site β) of the adjacent poly(N-acylalkylene imine) segment as indicated in the following general formula (6), and is a segment composed of a single $R^7SiO$ unit, a single $R^{11}$ and y+1 of $R^7{}_2SiO$ units. Also, "poly(N-acylalkylene imine) segment" means W bound to the above-described $R^{11}$.

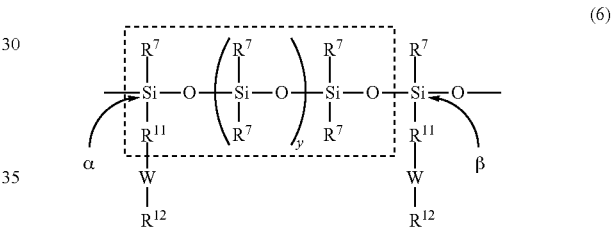

In the above-described general formula (6), each of $R^7$ independently represents alkyl group or phenyl group of 1 to 22 carbon atom(s), $R^{11}$ represents alkylene group containing hetero atom, W represents poly(N-acylalkylene imine) segment, $R^{12}$ represents residue of a polymerization initiator, and Y represents a positive number.

MWg is molecular weight of the section surrounded by the dotted line in the above-described general formula (6), and can be regarded as mass (g/mol) of organo polysiloxane segment per 1 mol of poly (N-acylalkylene imine) segment, and is identical to functional group equivalent (g/mol) of modified organo polysiloxane if 100% of functional groups of the modified organo polysiloxane that is a raw material compound are substituted with poly(N-acyl alkylene imine).

The molecular weight of poly (N-acylalkylene imine) segment (MWox), which can be measured by a method for calculating on the basis of the molecular weight and the polymerization degree of N-acylalkylene imine unit or by the gel permeation chromatography (GPC) measuring method as will be discussed later, is the number-average molecular weight measured by the GPC measuring method in the present invention, and is preferably $5.0 \times 10^2$ to $1.8 \times 10^3$, more preferably $7.0 \times 10^2$ to $1.5 \times 10^3$, and is even more preferably $8.0 \times 10^2$ to $1.4 \times 10^3$. This allows achieving further enhanced styling-abilities of both of the set-ability and the set-retention.

Also, MWg can be derived by the following formula (II) by employing the content ratio (Csi) of organo polysiloxane segment constituting the main chain.

$$MWg = \frac{Csi \times MWox}{100 - Csi} \quad (II)$$

The weight-average molecular weight of organo polysiloxane segment constituting the main chain (MWsi) is $1\times10^4$ to $1\times10^5$, and in view of providing enhanced smoothness of the hair while enhancing the volume of the hair and in view of further providing certain solubility in a polar solvent such as water and the like, and enhanced handling ability after the dissolution, such weight-average molecular weight is preferably $2\times10^4$ to $8\times10^4$, and is more preferably $5\times10^4$ to $8\times10^4$. Since it has the same skeleton as that of modified organo polysiloxane which is the raw material compound, MWsi is nearly the same as that of the mean molecular weight of modified organo polysiloxane.

In addition to above, the weight-average molecular weight of modified organo polysiloxane is the weight-average molecular weight in the polystyrene conversion measured with the following conditions by the GPC.
Column: Super HZ4000+Super HZ2000 (commercially available from Tosoh Co., Ltd.);
Eluent: 1 mM triethylamine/THF;
Flow rate: 0.35 mL/min.;
Column temperature: 40 degrees C.;
Detector: UV; and
Sample: 50 μL.

The weight-average molecular weight (MWt) of organo polysiloxane, in which a poly(N-acyl alkylene imine) segment composed of repeating units represented by the following general formula (1) is bound to at least two silicon atoms in organo polysiloxane segment constituting the main chain through alkylene group containing hetero atom, is preferably $1.2\times10^4$ to $1.5\times10^5$, and more preferably $2.4\times10^4$ to $1.2\times10^5$, and is even more preferably $3.7\times10^4$ to $9.2\times10^4$. This allows providing enhanced smoothness of the hair while enhancing the volume of the hair and in view of further providing enhanced solubility in a polar solvent such as water and the like. In the present Specification, MWt can be obtained from the weight-average molecular weight of the modified organo polysiloxane which is the raw material compound and the above-described mass ratio (a/b).

Also, the component (B) of the present invention is easily uniformly dissolved in the present aqueous cleansing agent, and more specifically, thus there is no need to employ a dissolution-assisting component such as an organic solvent and the like or a stabilizer.

The specific organo polysiloxane employed in the present invention may be employed alone, or a combination of two or more thereof may alternatively be employed.

Organo polysiloxane according to the present invention may be produced by a known method. For example, according to a method described in JA-A-H07-133,352 (1995), it is produced by reacting modified organo polysiloxane presented by the following general formula (7) with terminal reactive poly(N-acylalkylene imine) presented by the following general formula (8) obtainable by ring-opening polymerization of cyclic iminoether.

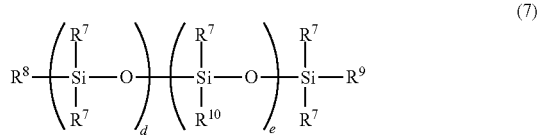

(7)

In the above-described general formula (7), $R^7$ is synonymous as represented above, and each of $R^8$ and $R^9$ represents the same group as $R^7$ or monovalent group expressed by any one of the following formulae (viii) to (xiii), d represents an integer number of 135 to 1,350, and e represents an integer number of 3 to 57.

$-(CH_2)_{\overline{3}}-NH_3$ (viii)

$-(CH_2)_{\overline{3}}-NH-(CH_2)_{\overline{2}}-NH_2$ (ix)

$-(CH_2)_{\overline{3}}-N(CH_3)_2$ (x)

$-(CH_2)_{\overline{3}}-N-(CH_2)_{\overline{2}}-N(CH_3)_2$ (xi)
         |
         $CH_3$ $-(CH_2)_{\overline{3}}-O-CH_2CHCH_2-N(CH_3)_2$ (xii)
                        |
                        OH $-(CH_2)_{\overline{3}}-SH$ (xii)

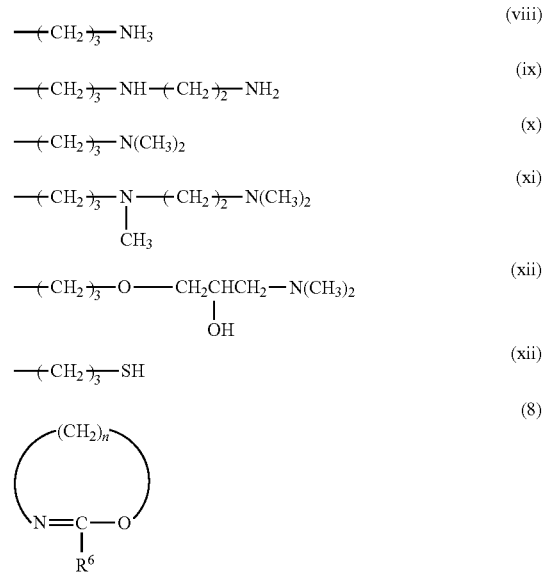

(8)

In the above-described general formula (8), $R^6$ and n are synonymous as represented in the above-described general formula (1).

Meanwhile, ring-opening polymerization of cyclic iminoether shown in the above-described general formula (8) can be conducted according to, for example, a method as described in Liebigs Ann. Chem., pp. 996 to pp. 1009 (1974). Compounds having higher electrophilic reactivity like alkyl esters of strong acids such as, for example, benzenesulfonic acid alkyl ester, p-toluenesulfonic acid alkyl ester, trifluoro methane sulfonic acid alkyl ester, trifluoro acetic acid alkyl ester, sulfuric acid dialkyl ester and the like may be employed for an initiator for the polymerization, and among these, sulfuric acid dialkyl is preferably employed. The quantity of the initiator for the use is ordinarily 1 mol over 2 to 100 mol of cyclic iminoether presented in the above-described general formula (8).

Available polymerization solvent includes, for example, acetate esters such as ethyl acetate, propyl acetate and the like; ethers such as diethyl ether, diisopropyl ether, dioxane, tetrahydrofuran and the like; ketones such as acetone, methyl ethyl ketone and the like; halogenated solvents such as chloroform, methylene chloride and the like; nitrile-based solvents such as acetonitrile, benzonitrile and the like; and non-proton polar solvent such as N,N-dimethylformamide, N,N-dimethylacetamide, dimethyl sulfoxide and the like, and among these, acetate esters are preferably used. The quantity of the solvent for the use is ordinarily 20 to 2,000 parts by mass over 100 parts by mass of cyclic iminoether presented in the above-described general formula (8).

The polymerization temperature is ordinarily 30 to 170 degrees C., preferably 40 to 150 degrees C., and the polymerization time is ordinarily 1 to 60 hours, though it is not constant according to polymerization temperature.

If, for example, 2-substituted-2-oxazoline is employed for cyclic iminoether represented in the above-described general formula (8), poly(N-acylethylenimine) (equivalent to n=2 in the above-described general formula (1)) is obtainable, and if 2-substituted-dihydro-2-oxazine is employed, poly(N-acyl propyleneimine) (equivalent to n=3 in the above-described general formula (1)) is obtainable. The molecular weight of terminal reactive poly(N-acylalkylene imine) is $8.0\times10^2$ to $1.6\times10^3$, more preferably $8.5\times10^2$ to $1.5\times10^3$, and is even more preferably $9.0\times10^2$ to $1.4\times10^3$.

It is preferable to employ modified organo polysiloxane having functional group equivalent of preferably 1,700 to 3,500, more preferably 1,800 to 3,200 and is even more preferably 2,000 to 3,000, and having the weight-average molecular weight of preferably $1.0\times10^4$ to $1.0\times10^5$, more preferably $2.0\times10^4$ to $8.0\times10^4$, and is even more preferably $3.0\times10^4$ to $6.0\times10^4$.

Typical method for bonding poly(N-acylalkylene imine) with organo polysiloxane segment is a method for reacting modified organo polysiloxane represented by the above-described general formula (7) with terminal reactive poly (N-acylalkylene imine), which is obtainable by conducting living polymerization of cyclic iminoether represented by the above-described general formula (8), which is a most effective method since the polymerization degree can be easily controlled by adjusting the using quantities of cyclic iminoether and polymerization initiator as described in theoretical equation (III) shown below (MWi; molecular weight of poly(N-acyl propyleneimine), and since poly(N-acyl alkylene imine) of nearly monodispersity and having narrower molecular weight distribution than that obtained by ordinary radical polymerization can be obtained.

$$MWi = \frac{\text{MOLE NUMBER OF CYCLIC IMINOETHER}}{\text{MOLE NUMBER OF POLYMERIZATION INITIATOR}} \times$$
$$\text{MOLECULAR RATIO OF CYCLIC IMINOETHER} +$$
$$\text{MOLECULAR WEIGHT OF POLYMERIZATION}$$
$$\text{INITIATOR}$$

(III)

The reaction of organo polysiloxane containing amino group with reactive end of poly(N-acylalkylene imine) obtained by living polymerization of cyclic iminoether may be, for example, conducted as follows. The initiator is dissolved in a single solvent of a polar solvent, preferably acetonitrile, valeronitrile, dimethyl formamide, dimethyl acetamide, chloroform, methylene chloride, ethylene chloride, ethyl acetate, methyl acetate and the like, or a mixed solvent thereof with other solvent as required, and the temperature is elevated to 40 to 150 degrees C., preferably 60 to 100 degrees C. Cyclic iminoether represented by the above-described general formula (8) is supplied thereto at one time, or by drops when the reaction is intense, to carry out the polymerization. Progress of the polymerization can be traced by conducting quantification for the amount of the remained cyclic iminoether that is a monomer by employing an analytical instrument such as a gas chromatography or the like. Even if cyclic imino ether is consumed to terminate the polymerization, active species of the growing end maintains its reactivity. Ongoingly, this polymer solution is mixed with organo polysiloxane containing amino group in its molecule without isolating polymer to carry out the reaction under the conditions of 5 to 100 degrees C., preferably 20 to 60 degrees C. While the mixing ratio can be suitably selected as desired, it is preferable to carry out the reaction at a ratio of 0.1 to 1.3 mol equivalent of Poly (N-acyl alkylene imine) per 1 mol of amino group in organo polysiloxane. Block copolymer or graft polymer, in which poly(N-acylalkylene imine) segment is bonded to poly dimethyl siloxane, can be obtained by the above-described reaction.

Specific examples of organo polysiloxanes obtainable by the above process include poly(N-formyl ethylene imine) organosiloxane, poly(N-acetyl ethylene imine) organosiloxane and poly(N-propionyl ethylene imine) organosiloxane. It is preferable to employ one or two or more selected from the above-described organo polysiloxanes.

Also, concerning the storage elastic modulus and the adhesion of the organo polysiloxane obtainable by the above process, it is found by the investigations of the present inventors that the storage elastic modulus tends to be reduced when the silicone content is larger and the adhesion tends to be increased when length of oxazoline chain is shorter. Therefore, the product having the storage elastic modulus and the adhesion having the specific ranges can be obtained by adjusting oxazoline chain length and the silicone content of the above-described organo polysiloxane, so that such organo polysiloxane can be selectively employed as the component (B). Such specific organo polysiloxane is employed as the component (B) to further stably obtain the conditioning effect and the volume-up effect.

On the other hand, in general, silicones have larger number of variations, and the physical properties of those are considerably different by those structures or polymerization degrees. A silicone gum exhibiting higher polymerization and higher viscosity, typically, for example, TSE200A (commercially available from Toshiba silicone Co., Ltd.), exhibits higher adhesion of 270 gf according to the measurement of the present inventors, but also exhibits the storage elastic modulus of $4\times10^4$ Pa at 20 degrees C., $3\times10^4$ Pa at 40 degrees C., and $2.5\times10^4$ Pa at 80 degrees C., which are different from those of the component (B) according to the present invention.

Also, other examples of the modified silicone include, for example, modified silicones discussed later in reference to Table 1 in the section of Example, and the storage elastic modulus thereof are also different from that of the component (B) as shown in table 1.

The contained amount of the component (B), in view of further firmly obtaining the volume-up effect after drying, may be, for example, equal to or higher than 0.05% by mass over the whole aqueous hair cleansing agent, and is preferably equal to or higher than 0.1% by mass, and is even more preferably equal to or higher than 0.2% by mass. On the other hand, in view of residue feel, the contained amount of the component (B) may be, for example, equal to or lower than 4% by mass over the whole aqueous hair cleansing agent, and is preferably equal to or lower than 3% by mass, and is even more preferably equal to or lower than 2% by mass. To summarize these aspects, the amount of the component (B) in the aqueous hair cleansing agent is preferably within a range from 0.05 to 4% by mass, more preferably within a range from 0.1 to 3% by mass, and even more preferably a range from 0.2 to 2% by mass.

(Component (C))

The component (C) is one or more of cationized polymer(s) selected from (c-1) and (c-2).

(c-1) a cationized polymer having cellulose skeleton or galactomannan skeleton; and (c-2) a cationic polymer having diallyl dimethylammonium salt skeleton.

For the (c-1) polymer, one, two or more selected from sugar-based cationic polymers having cellulose skeleton or galactomannan skeleton may be employed. The (c-1) polymer is, more specifically, natural-type cationized polymer.

For the cationized polymer having cellulose skeleton, one, two or more selected among cationized cellulose derivatives may be employed. More specifically, cationized cellulose, cationized hydroxyethyl cellulose, cationized carboxymethyl cellulose, cationized hydroxypropyl cellulose and the like are exemplified. Among these, in view of reducing the stickiness and the squeaky feel of the hair in the rinsing, it is preferable to employ cationized hydroxyethyl cellulose.

Also, for the cationized polymer having galactomannan skeleton, one, two or more selected from cationized guar gum, cationized locust bean gum, cationized tara gum, cationized cassia gum and cationized fenugreek gum may be employed. Among these, galactomannan is preferable. Further, cationized galactomannan having ratio of galactose and mannose of 1:2 to 1:4 is further preferable. More specifically, it is one or more selected from the group consisting of cationized guar gum, cationized tara gum and cationized locust bean. Among these, in view of providing natural hairstyle and stably obtaining volume-up effect of the hair after drying, cationized guar gum is more preferable. Cationized galactomannan is a water-soluble cationized polymer, in which quaternary nitrogen-containing group is introduced into galactomannan composed of main chain having mannose structural unit and side chains of galactose unit. Galactomannans are, for example, obtainable from albumen in the seed of Leguminosae plants. It can be classified that the component having the ratio of galactose and mannose of 1:2 is guar gum; that of 1:3 is tara gum; and that of 1:4 is locust bean gum.

Preferable (c-1) polymer is one or more selected from cationized cellulose, cationized hydroxyethyl cellulose and cationized guar gum.

On the other hand, the composing monomer for (c-2) cationic polymer having diallyl dimethylammonium salt skeleton contains diallyl dimethylammonium salt as indispensable component. The (c-2) polymer is, more specifically, a synthesis cationized polymer. More specifically, this typically includes a homopolymer composed of diallyl dimethylammonium salt skeleton, or besides this composing monomer, binary or ternary cationized polymer obtained by copolymerization of the composing monomers such as (meta)acrylic acid or (meta)acrylamide and the like. For example, this typically includes a binary polymer composed of diallyl dimethylammonium salt/(meta)acrylic acid or (meta)acrylamide or a ternary polymer composed of diallyl dimethylammonium salt/(meta)acrylate/(meta)acrylamide. It is needless to point out that other composing monomer may be contained, and the type of the composing monomer is not limited. However, in view of maintaining the smoothness of the hair in the wetting condition or in rinsing, vinyl pyrrolidone and ethyleneimine are not preferable.

For the (C) component, any one of cationized guar gum, cationized locust bean gum, cationized hydroxyethyl cellulose and dimethyl diallyl ammonium chloride-acrylamide copolymer is preferable. This is because: cationized guar gum is preferable in view of providing voluminous hair after drying; diallyl dimethylammonium copolymer is preferable in view of absence of coarse or rough feel after drying; and cationized hydroxy cellulose is preferable in view of absence of the residue feel after drying.

Among the (C) components, the commercially available products of cationized guar gum for the commercially available product of (c-1) cationized galactomannan typically includes Jaguar series products such as Jaguar C-13S, Jaguar C-14S, Jaguar C-17 and the like (commercially available from Rhodia, guar hydroxypropyl triammonium chloride). Also, the commercially available product of cationized tara gum typically includes Catinal CTR-100, Catinal CTR-200 (commercially available from Toho Chemical Industry Co., Ltd.) and the like. Also, the commercially available product of cationized locust bean gum typically includes Catinal CLB-100 (commercially available from Toho Chemical Industry Co., Ltd. locust bean hydroxypropyl trimonium chloride) and the like.

Also, the commercially available product of the (c-2) diallyl dimethylammonium salt of the (C) component includes: Merquat 550 (commercially available from The Lubrizol Corporation, copolymer of acrylamide and diallyl dimethylammonium salt; CFTA name: polyquarternium-7); Ucare polymer JR series and ditto LR series (commercially available from Amerchol, salt of reactant of trimethyl ammonium substituted epoxide and hydroxyethyl cellulose; CFTA name: polyquaternium-10); and Poiz C-60H, Poiz C-80M and Poiz C-150L (Commercially available from Kao Co., Ltd., salt of reactant of trimethyl ammonium-substituted epoxide and hydroxyethyl cellulose: CFTA name: polyquaternium-10) and the like.

Among the component of (c-1) and (c-2), (c-1) cationized polymer is preferable in view of providing the smoothness after the treatment to the hair with the composition.

These polymers may be employed alone, or a combination of two or more of these may be employed.

The content of the component (c-1) polymer is, in view of reducing the squeaky feel of the hair in rinsing, for example equal to or higher than 0.01% by mass over the whole aqueous hair cleansing agent, and is preferably equal to or higher than 0.05% by mass, and is further preferably equal to or higher than 0.1% by mass.

Also, in view of balancing between the improvement of the foaming and the depression of the residue feel after drying, the content of the component (C) may be, for example, equal to or lower than 3% by mass over the whole aqueous hair cleansing agent, preferably equal to or lower than 1.5% by mass, and is further preferably equal to or lower than 1.0% by mass, and it may be is equal to or lower than 0.5% by mass.

The component (c-2) polymer may be employed alone, or a combination thereof may be employed, and in view of reducing the squeaky feel of the hair in rinsing, the content thereof may be equal to or higher than 0.01% by mass, and be preferably equal to or higher than 0.02% by mass, and is further preferably equal to or higher than 0.05% by mass. Also, from the viewpoint of the quality of foam, it may be equal to or lower than 3% by mass, and is preferably equal to or lower than 2% by mass, and it is more preferably equal to or lower than 1% by mass. To summarize these points of view, in view of reducing the squeaky feel of the hair in rinsing, the content thereof may be, for example, within the range from 0.01 to 3% by mass over the whole aqueous hair cleansing agent of the present invention, preferably within the range from 0.02 to 2% by mass, and is more preferably within the range from 0.05 to 1% by mass.

These components may be employed alone, or a combination of two or more of these may be employed.

The content of the component (C) in that case may be, in view of reducing the squeaky feel of the hair in rinsing, for example equal to or higher than 0.01% by mass over the whole aqueous hair cleansing agent, preferably equal to or higher than 0.05% by mass, and is even more preferably equal to or higher than 0.1% by mass.

On the other hand, in view of balancing between the improvement of foaming property and the depression of the residue feel after drying, the content of the component (C) may be, for example, equal to or lower than 3% by mass over the whole aqueous hair cleansing agent, and is preferably equal to or lower than 1.5% by mass, and is even more preferably equal to or lower than 1.0% by mass, and may also be preferably equal to or lower than 0.5% by mass.

Also, the mass ratio (component (B)/component (C)) of the component (B) for the component (C) of the aqueous hair cleansing agent according to the present invention may be equal to or higher than 0.2 in view of improving the stability of the foam and firmly obtaining the volume-up effect after drying, and is preferably equal to or higher than 0.5, and is even more preferably equal to or higher than 1. On the other hand, in view of balancing between enhancement in the forming and quickness to rinse off and depression of the residue feel in rinsing, the ratio [component (B)/component (C)] in the aqueous hair cleansing agent according to the present invention may be, for example, equal to or lower than 15, and is preferably equal to or lower than 10, and is further preferably equal to or lower than 5.

In the next, a method for producing the aqueous hair cleansing agent according to the present invention will be described.

There is no limitation in the method for producing the aqueous hair cleansing agent according to the present invention, and for example, may be obtainable by adding the above-described components (A) to (C), water, and other components as required, preferably in a predetermined sequence.

In the aqueous hair cleansing agent of the present invention, the combination of the above-described components (A) to (C) is employed to reduce the residue feel such as the stickiness or the like and the weighing-down due to the weight of the agent, so that enhanced volume-up effect can be obtained and sufficient conditioning effect can be obtained. Although the reason for the foregoing is not necessarily clear, it can be considered that the component (C) coacervates in rinsing so that the composite is precipitated on the hair surface, allowing the component (B) remaining on the hair surface after rinsing, and can also be considered that the component (B) has specific properties of the storage elastic modulus and the adhesion so that both of the enhanced volume-up effect and the smooth and natural finish without stickiness can be compatibly achieved.

Also, the combination of the above-described components (A) to (C) is employed to allow, for example, enhancing the height of hair at the top, the lift up of a front hair, or overall airy (fluffy) texture, while maintaining sufficient foaming. This can also achieve, for example, even feel of the hair surface, natural and light smoothness, shiny, three-dimensional hair or manageability effect.

In the aqueous hair cleansing agent according to the present invention, in view of suppressing the stiff feel and the remaining feel after drying, and in view of providing natural hairstyle and stably obtaining the volume-up effect of the hair after drying, the formulation of the components (A) to (C) is, for example, the content of the component (A) is 1 to 30% by mass, the content of the above-described component (B) is 0.05 to 4% by mass, and the content of the above-described component (C) is 0.01 to 3% by mass. Also, it is preferable that the content of the component (A) is 5 to 25% by mass, the content of the component (B) is 0.1 to 3% by mass, and the content of the component (C) is 0.05 to 2% by mass, and it is more preferable that the content of the component (A) is 7 to 15% by mass, the content of the component (B) is 0.2 to 2% by mass, and the content of the component (C) is 0.1 to 1% by mass.

Also, the content of water is preferably 50 to 95% by mass in the aqueous hair cleansing agent of the present invention, and more preferably 60 to 90% by mass.

It is preferable that the aqueous hair cleansing agent of the present invention contains an inorganic salt as one of the salts. More specifically, one, two or more selected sodium chloride, sodium sulfate, sodium phosphate, potassium chloride, potassium sulfate and potassium phosphate may be employed. In view of stably obtaining natural hairstyle, absence of residue feel after drying and volume-up effect of the hair, sodium chloride and sodium sulfate are more preferable, and sodium chloride is even more preferable.

One of these salts may be employed alone, or a combination of two or more thereof may also be employed, and the content in the aqueous hair cleansing agent is, for example, equal to or higher than 0.01% by mass in view of exhibiting the above-described effects, and is preferably equal to or higher than 0.05% by mass, and is even more preferably equal to or higher than 0.1% by mass. On the other hand, in viewpoint of creating foam in the use, the content of salts is, for example, equal to or lower than 2% by mass, in the aqueous hair cleansing agent, and is preferably equal to or lower than 1.5% by mass, and is even more preferably equal to or lower than 1% by mass. To summarize these points of view, the content of the salts is preferably within the range from 0.01 to 2% by mass in the aqueous hair cleansing agent of the present invention, and more preferably within the range from 0.05 to 1.5% by mass, and is even more preferably within the range from 0.1 to 1% by mass.

Also, the aqueous hair cleansing agent of the present invention may be configured to further contain one or more of alcohol(s) selected from the group consisting of benzyl alcohol and polypropylene glycol, from the viewpoint of the manageability of the hair and the volume-up effect of the hair. Typical polypropylene glycol available here includes, for example, polypropylene glycol having number average molecular weight of 100 to 1,000, and is preferably having number average molecular weight of 300 to 500. Here, the number average molecular weight means number average molecular weight of polystyrene conversion measured by GPC.

Two or more of alcohols may be used together in the aqueous hair cleansing agent, and the total content thereof is, for example, preferably 0.01 to 5% by mass over the whole aqueous hair cleansing agent, in view of manageability of the hair, volume-up effect of the hair, and enhancing the tensile and the resilience of the hair, and more preferably 0.1 to 5% by mass.

Also, the aqueous hair cleansing agent of the present invention preferably exhibits pH when being applied over the hair (diluted 20 mass-times with water, 25 degrees C.) of 2 to 8, in view improving the gloss and the manageability of the hair, and is more preferably 3 to 7.

Typical pH adjuster includes organic carboxylic acid of 2 to 8 carbon atoms, and more specifically hydroxy monocarboxylic acid and dicarboxylic acid. Specific examples of hydroxy monocarboxylic acid include glycolic acid, lactic acid, glyceric acid, gluconic acid, pantothenic acid and the like. Specific examples of dicarboxylic acid include malic acid, oxalic acid, malonic acid, maleic acid, succinic acid, glutaric acid and the like. It is preferable to employ one, two or more selected from the above-described organic carboxylic acids. Further, in view of improving the creation of foam in the condition of acidity and providing the volume-up effect, glycolic acid, lactic acid and malic acid are preferable, and lactic acid and malic acid are more preferable.

Two or more of the above-described organic acids may be employed together. The content of organic carboxylic acid of 2 to 8 carbon atoms in the aqueous hair cleansing agent is, in view of the gloss of the hair, equal to or higher than 0.01% by mass, preferably equal to or higher than 0.05% by mass, and is more preferably equal to or higher than 0.1% by mass. On the other hand, the content of organic carboxylic acid of 2 to 8 carbon atoms in the aqueous hair cleansing agent is, in view of improving the manageability, equal to or lower than 5% by mass, preferably equal to or lower than 3% by mass, and is more preferably equal to or lower than 2% by mass. To summarize these aspects, it is preferable that the content of organic carboxylic acid of 2 to 8 carbon atoms is within the range from 0.01 to 5% by mass in the aqueous hair cleansing agent of the present invention, in view of achieving improved gloss and manageability of the hair. It is more preferably within the range from 0.05 to 3% by mass, and is more preferably within the range from 0.1 to 2% by mass.

Also, base such as sodium hydroxide, potassium hydroxide, ammonium chloride and the like may be employed as other pH adjuster, in combination with these organic carboxylic acids.

The aqueous hair cleansing agent according to the present invention may further contain a component except the above-described components (A) to (C) and water. For example, the aqueous hair cleansing agent according to the present invention may be configured to contain a cationized polymer except the component (C). Typical cationized polymer except the component (C) includes: cationic starch; copolymers such as vinyl imidazolium trichloride/vinyl pyrrolidone copolymer, hydroxy ethyl cellulose/dimethyl diallyl ammonium chloride copolymer, vinyl pyrrolidone/quaternized dimethyl aminoethyl methacrylate copolymer, poly vinyl pyrrolidone/alkyl amino acrylate copolymer, poly vinyl pyrrolidone/alkylamino acrylate/vinyl caprolactam copolymer, vinyl pyrrolidone/methacrylic amidepropyl trimethylammonium chloride copolymer, alkyl acrylamide/acrylate/alkyl amino alkyl acrylamide/polyethylene glycol methacrylate copolymer, adipic acid/dimethyl amino hydroxypropyl ethylene triamine copolymer (commercially available from Sandoz in United States of America, Cartaretin) and the like; cationic polymer described in Japanese Patent Laid-Open No. S53-139,734 (1978); cationic polymer described in Japanese Patent Laid-Open No. S60-36,407 (1985) and the like.

Also, other commercially available products, which can be employed as the cationized polymer except the component (C) typical includes: CFTA name: polyquaternium-7); Luviquat FC370 (commercially available from BASF AG, copolymer of 1-vinyl-2-pyrrolidone and 1-vinyl-3-methylimidazolium salt; CFTA name: polyquaternium-16) and the like.

One of the cationized polymer except the component (C) may be employed alone, or a combination of two or more thereof may be employed, and in view of reducing the squeaky feel of the hair in rinsing, the content thereof is, for example, 0.01 to 3% by mass over the whole aqueous hair cleansing agent of the present invention, preferably 0.02 to 2% by mass, and is more preferably 0.05 to 1% by mass.

In order to further improve the cleansing performance, a nonionic surfactant or an ampholytic surfactant may be contained in the aqueous hair cleansing agent according to the present invention. It is preferable to employ one, two or more selected from the following nonionic surfactant or ampholytic surfactant.

Typical available nonionic surfactant include: polyoxyalkylene sorbitan fatty acid esters, polyoxyalkylene sorbitol fatty acid esters, polyoxyalkylene glycerol fatty acid esters, polyoxyalkylene fatty acid esters, polyoxyalkylene alkyl ethers, polyoxyalkylene alkyl phenyl ethers, polyoxyalkylene (hydrogenated) castor oils, saccharose fatty acid esters, polyglycerol alkylethers, fatty acid polyglycerides, fatty acid alkanolamide, alkyl glycosides, monoalkenyl glyceryl ethers and the like.

Among these, polyoxyalkylene sorbitan fatty acid esters such as polyoxyethylene sorbitan fatty acid ester and the like, polyoxyalkylene fatty acid esters such as polyoxyalkylene (C8 to C20) fatty acid ester and the like, polyoxyalkylene (hydrogenated) castor oils such as polyoxyethylene hydrogenated castor oil and the like, and alkyl glycosides are preferable.

Fatty acid alkanolamide is also preferable, and either of mono alkanol amide and dialkanol amide may be employed, and it is preferable to have acyl group of 8 to 18 carbon atoms and is further preferable to have 10 to 16 carbon atoms. It is also preferable to have hydroxyalkyl group of 2 to 3 carbon atoms, and for example, typical example includes: oleic diethanolamide, palm kernel oil fatty acid diethanolamide, coconut oil fatty acid diethanolamide, lauric diethanolamide, polyoxyethylene coconut oil fatty acid monoethanol amide, coconut oil fatty acid monoethanol amide, lauric isopropanol amide, lauric monoethanol amide and the like.

Typical ampholytic surfactant includes betaine-based surfactants. Among these, alkyl dimethyl amino acetic acid betaine, fatty acid amide propyl betaine, alkyl hydroxy sulfobetaine and the like are more preferable, and fatty acid amide propyl betaine is even more preferable. It is preferable that fatty acid amide propyl betaine has acyl group of 8 to 18 carbon atoms, and more preferably 10 to 16 carbon atoms, and lauric amide propyl betaine, palm kernel oil fatty acid amide propyl betaine, coconut oil fatty acid amide propyl betaine and the like are even more preferable.

In addition, other ampholytic surfactant includes sultaine-based surfactants such as lauryl hydroxy sultaine and the like.

One of these nonionic surfactant or ampholytic surfactant may be employed alone, or a combination of two or more thereof may also be employed in the aqueous hair cleansing agent. When the aqueous hair cleansing agent of the present invention is presented in a form of an aqueous liquid cleansing agent, it is more preferable to employ fatty acid amide propyl betaine, fatty acid alkanolamide or mono alkyl glyceryl ether together with component (A) since this achieves not only enhanced foaming force but also appropriate liquid characteristics.

The content of the nonionic surfactant or the ampholytic surfactant in the aqueous hair cleansing agent is equal to or higher than 0.01% by mass in view of achieving improved effect of enhancing foam, and is preferably equal to or higher than 0.05% by mass, and is further preferably equal to or higher than 0.1% by mass. In view of achieving improved effect of enhancing foam and the stability, it is equal to or lower than 10% by mass, preferably equal to or lower than 6% by mass, and is further preferably equal to or lower than 4% by mass. To summarize these aspects, the content of nonionic surfactant or ampholytic surfactant may be, for example, 0.01 to 10% by mass over the whole aqueous hair cleansing agent according to the present invention, in view of achieving improved effect of enhancing foam, and is preferably 0.05 to 6% by mass, is more preferably 0.1 to 4% by mass.

Further, a cationized surfactant or a silicone except for the component (B) may be further contained in the aqueous hair cleansing agent according to the present invention, in order to achieve improved finish after drying.

Typical cationized surfactant includes, for example, (xxi) alkyl trimethylammonium salt, (xxii) alkoxy trimethylammonium salt, (xxiii) dialkyl dimethylammonium salt, (xxiv) alkyl dimethylamine and its salts, (xxv) alkoxy dimethylamine and its salts, (xxvi) alkylamide dimethylamine and its salts and the like.

(xxi) Alkyl Trimethylammonium Salt

Typical alkyl trimethylammonium salt includes, for example, a compound represented by the following general formula.

$$R^{22}-N^{+}(CH_3)_3 Z^{-}$$

In the above-described formula, $R^{22}$ represents alkyl group of 12 to 22 carbon atoms, $Z^{-}$ represents halide ion such as chloride ion, bromide ion and the like.

More specifically, cetyl trimethylammonium chloride, stearyl trimethylammonium chloride, behenyl trimethylammonium chloride and the like are exemplified.

(xxii) Alkoxy Trimethylammonium Salt

Typical alkoxy trimethylammonium salt includes, for example, a compound represented by the following general formula.

$$R^{23}-O-R^{24}-N^{+}(CH_3)_3 Z^{-}$$

In the above-described formula, $R^{23}$ represents alkyl group of 12 to 22 carbon atoms, $R^{24}$ represents ethylene group or propylene group, which may be substituted with hydroxy group, and $Z^{-}$ is the same as described above.

More specifically, stearoxy propyl trimethylammonium chloride, stearoxy ethyl trimethylammonium chloride, stearoxy hydroxypropyl trimethylammonium chloride and the like may be exemplified.

(xxiii) Dialkyl Dimethylammonium Salt

Typical dialkyl dimethylammonium salt includes, for example, a compound represented by the following general formula.

$$(R^{25})_2 N^{+}(CH_3)_2 Z^{-}$$

In the above-described formula, $R^{25}$ represents, independently, alkyl group or benzyl group of 12 to 22 carbon atoms, and $Z^{-}$ is the same as described above.

More specifically, distearyl dimethylammonium chloride and the like may be exemplified.

(xxiv) Alkyl Dimethylamine and its Salt

Alkyl dimethylamine and its salt include, for example, a compound represented by the following general formula and its salts.

$$R^{26}-N(CH_3)_2$$

In the above-described formula, $R^{26}$ represents alkyl group of 12 to 22 carbon atoms.

More specifically, behenyl dimethylamine, stearyl dimethylamine and organic acid salt thereof and the like may be exemplified.

(xxv) Alkoxy Dimethylamine and its Salt

Alkoxy dimethylamine and its salt include, for example, a compound represented by the following general formula and its salts.

$$R^{27}-O-R^{a}-N(CH_3)_2$$

In the above-described formula, $R^{27}$ represents alkyl group of 12 to 22 carbon atoms, and $R^{28}$ represents ethylene group or propylene group.

(xxvi) Alkylamide Dimethylamine and its Salt

Alkylamide dimethylamine and its salt include, for example, a compound represented by the following general formula and its salts.

$$R^{29}-C(=O)NH-R^{30}-N(CH_3)_2$$

In the above-described formula, $R^{29}$ represents alkyl group of 11 to 21 carbon atoms, and $R^{30}$ represents ethylene group or propylene group.

Cationized surfactants except the above-described compounds (xxi) to (xxvi) include:
lanolin fatty acid aminopropyl ethyl dimethylammonium ethylsulfate (ethylsulfate salt of alkanoyl aminopropyl dimethyl ethyl ammonium, alkanoyl group is derived from lanolin); lanolin fatty acid amino ethyl triethyl ammonium ethylsulfate; lanolin fatty acid amino propyl triethyl ammonium ethylsulfate; lanolin fatty acid amino ethyl trimethyl ammonium methylsulfate; lanolin fatty acid amino propyl ethyl dimethylammonium methylsulfate; isoalkanoic acid (C14 to C20) aminopropyl ethyl dimethylammonium ethylsulfate; isoalkanoic acid (C18 to C22) aminopropyl ethyl dimethylammonium ethylsulfate; aminopropyl ethyl dimethylammonium isostearate ethylsulfate; aminopropyl ethyl dimethylammonium isononanoate ethylsulfate, and alkyl trimethylammonium saccharin and the like.

One of the cationized surfactants may be employed alone, or a combination of two or more thereof may also be employed together, and is equal to or higher than 0.01% by mass in the aqueous hair cleansing agent, in view of achieving the smoothness from the shampooing to the rinsing, and is preferably equal to or higher than 0.02% by mass, and is even more preferably equal to or higher than 0.05% by mass, and on the other hand, in view of foaming, it is, for example, equal to or lower than 3% by mass, and is preferably equal to or lower than 1% by mass, and is even more preferably equal to or lower than 0.1% by mass. To summarize these aspects, in view of achieving the smoothness from the shampooing to the rinsing, the content of the cationized surfactant is preferably 0.01 to 3% by mass in the aqueous hair cleansing agent of the present invention, and is even more preferably 0.02 to 1% by mass, and in view of foaming, 0.05 to 0.1% by mass is preferable, and it is preferable to substantially contain none of these.

Typical silicones except the component (B) include dimethyl polysiloxane, polyether-modified silicone, amino-modified silicone, carboxy-modified silicone, methyl phenyl polysiloxane, fatty acid-modified silicone, alcohol-modified silicone, aliphatic alcohol-modified silicone, epoxy-modified silicone, fluorine-modified silicone, cyclic silicone, alkyl-modified silicone and the like. Among these, dimethyl polysiloxane, polyether-modified silicone and amino-modified silicone are preferable.

Among these, dimethyl polysiloxane is capable of providing enhanced lubricity over the hair, polyether-modified silicone is capable of providing the smoothness over the hair, and amino-modified silicone is capable of providing moist feel over the hair. In the present invention, one of various types of silicones may be employed alone, or a combination of two or more thereof may be employed according to the required performances. Dimethyl polysiloxanes available here includes various compositions ranging from that exhibits viscosity of about 5 mm$^2$/s to that exhibits viscosity of about 10,000,000 mm$^2$/s, which is often supplied as an emulsion according to the required feel, and the compositions exhibiting viscosity of 5,000 to 10,000,000 mm$^2$/s are preferable, and the compositions exhibiting viscosity of 50,000 to 10,000,000 mm$^2$/s are further preferable.

It is sufficient that polyether-modified silicone is a silicone having polyoxyalkylene group, and typical group constituting polyoxyalkylene group includes oxyethylene group and oxypropylene group. More specifically, typical silicones includes, for example, KF-6015, KF-945A, KF-6005, KF-6009, KF-6013, KF-6019, KF-6029, KF-6017, KF-6043, KF-353A, KF-354A, KF-355A (all the above are commercially available from Shin-Etsu Chemical Co., Ltd.), FZ-2404, SS-2805, FZ-2411, FZ-2412, SH3771M, SH3772M, SH3773M, SH3775M, SH3749, SS-280X series, BY22-008M, BY11-030 and BY25-337. (all the above are commercially available from Dow Corning Toray Co., Ltd.)

Preferable amino-modified silicone typically include silicone having mean molecular weight of about $3 \times 10^3$ to $1 \times 10^5$, described by the name of Amodimethicone in CFTA dictionary (U.S.A., Cosmetic Ingredient Dictionary), the third edition. Commercially available products thereof include SM 8704C (commercially available from Dow Corning Toray Co., Ltd.), DC 929 (commercially available from Dow Corning), KT 1989 (commercially available from GE Toshiba Silicone Co., Ltd.), 8500 Conditioning Agent, DOW CORNING TORAY SS-3588, DOW CORNING TORAY SILSTYLE 104 (commercially available from Dow Corning Toray Co., Ltd.) and the like.

The content of the silicones except the component (B) is equal to or higher than 0.05% by mass in the aqueous hair cleansing agent from the viewpoint of the finger-combing smoothness after shampooing, and is preferably equal to or higher than 0.1% by mass, and even more preferably equal to or higher than 0.5% by mass, and on the other hand, is, for example, equal to or lower than 20% by mass from the viewpoint of reduced stickiness feel, and is preferably equal to or lower than 10% by mass, and is even more preferably equal to or lower than 5% by mass. To summarize these aspects, the content of the silicones except the component (B) is preferably within a range from 0.05 to 20% by mass in the aqueous hair cleansing agent of the present invention, in view of the finger-comb smoothness and reduced stickiness feel, and is more preferably within a range from 0.1 to 10% by mass, and is even more preferably within a range from 0.5 to 5% by mass.

The aqueous hair cleansing agent according to the present invention may further contain ethylene glycol mono fatty acid ester, ethylene glycol difatty acid ester, or, pearlescent agent containing ethylene glycol monoalkyl ether or ethylene glycol dialkyl ether.

Typical ethylene glycol mono fatty acid ester includes ethylene glycol monostearic acid ester, ethylene glycol mono behenic acid ester and the like, and typical ethylene glycol difatty acid ester includes ethylene glycol distearyl ester, ethylene glycol dibehenyl ester and the like. Typical ethylene glycol monoalkyl ether includes ethylene glycol mono stearyl ether and the like. In addition, typical ethylene glycol dialkyl ether includes ethylene glycol distearyl ether and the like.

One of these may be employed alone, or two or more may be jointly employed, and the content thereof is equal to or higher than 0.1% by mass in the aqueous hair cleansing agent, in view of enhancement of the smoothness in rinsing, and is preferably equal to or higher than 0.2% by mass, and even more preferably equal to or higher than 0.5% by mass, and on the other hand, in view of improvement of the storage stability, is equal to or lower than 10% by mass, and is preferably equal to or lower than 5% by mass, and is even more preferably equal to or lower than 4% by mass. To summarize these aspects, the content of the above-described pearlescent agent is, in view of the improvement of the storage stability of the aqueous hair cleansing agent and in view of the improvement of the smoothness in creating foam and in rinsing, preferably within the range from 0.1 to 10% by mass of the aqueous hair cleansing agent of the present invention, and is more preferably within the range from 0.2 to 5% by mass, and is even more preferably within the range from 0.5 to 4% by mass.

In addition, the aqueous hair cleansing agent of the present invention may additionally contain an oil agent as other conditioning agent. Typical oil agent includes: hydrocarbons such as squalene, scualane, liquid paraffin, liquid isoparaffin, cycloparaffin and the like; glycerides such as castor oil, cacao oil, mink oil, avocado oil, olive oil, sunflower oil, camellia oil and the like; waxes such as beeswax, whale wax, lanolin, carnauba wax and the like; alcohols such as cetyl alcohol, oleyl alcohol, stearyl alcohol, isostearyl alcohol, 2-octyl dodecanol, glycerol, myristyl alcohol, behenyl alcohol, cetostearyl alcohol and the like; esters such as isopropyl palmitate, isopropyl myristate, octyl dodecyl myristate, hexyl laurate, cetyl lactate, propyleneglycol monostearate, oleyl oleate, hexadecyl 2-ethylhexanoate, isononyl isononanoate, tridecyl isononanoate and the like; higher fatty acids such as capric acid, lauric acid, myristic acid, palmitic acid, stearic acid, behenic acid, oleic acid, coconut oil fatty acid, isostearyl acid, isopalmitic acid and the like; and in addition, isostearyl glyceryl ether, polyoxypropylene butyl ether and the like. Among these, higher alcohols are preferable, and myristyl alcohol, cetyl alcohol, stearyl alcohol, sunflower oil, and camellia oil are more preferable.

One of these oil agents may be employed alone, or a combination of two or more thereof may also be employed, and the content thereof is equal to or higher than 0.001% by mass in view of the conditioning effect for the hair in the aqueous hair cleansing agent of the present invention, and is preferably equal to or higher than 0.005% by mass, and is even more preferably equal to or higher than 0.01% by mass, and on the other hand, in view of the stickiness of the hair, is equal to or lower than 2% by mass, and is preferably equal to or lower than 1.5% by mass, and is even more preferably equal to or lower than 1% by mass. To summarize these aspects, the content of the oil agent in the aqueous hair cleansing agent is preferably within the range from 0.001 to 2% by mass, and is more preferably within the range from 0.005 to 1.5% by mass, and is even more preferably within the range from 0.01 to 1% by mass.

In the aqueous hair cleansing agent of the present invention, in addition to the above-described components, components which are commonly employed for ordinary aqueous hair cleansing agents, may be suitably blended according to the purposes. Such arbitrary component may includes, for example: anti-dandruff agent; vitamin agent; disinfecting agent; anti-inflammatory agent such as glycyrrhizinic acid, glycyrrhetinic acid and derivatives thereof and the like; antiseptic agent; chelate agent; moisturizing agent such as sorbitol, panthenol and the like; coloring agent such as dye, pigment and the like; essence or extractives such as polar solvent-extract of eucalyptus, protein obtained from shell having nacreous layer or pearl or hydrolysate thereof, honey, royal jelly, protein obtained from silk or hydrolysate thereof, protein-containing extract obtained from seed of Leguminosae plant, Asian ginseng extract, rice germ extract, fucus extract, aloe extract, lotus extract, pomegranate extract, rose hip extract, chamomilla extract, licorice extract, alpinia speciosa leaf extract, chlorella extract and the like; pearlescent agent except the above-described components such as titanium oxide and the like; perfume; pigment;

ultraviolet absorber; antioxidant; shea butter; rose water; orange oil; eucalyptus oil and the like. The aqueous hair cleansing agent of the present invention is produced by dissolving a mixture of the components (A) to (C) and other components in water.

The conformation of the aqueous hair cleansing agent of the present invention may be suitably selected from liquid, gel and the like, and preferably liquid with a solvent of water or lower alcohol, and further preferably liquid with water.

The present invention is not limited to the above-described embodiments, and modifications and improvements within the range that can achieve the purposes of the present invention are included in the scope of the present invention.

For example, the present invention includes the following specific forms:
use of the above-described aqueous hair cleansing agent according to the present invention for applying over scalp and then foaming, rinsing and drying.

The above-described drying may be conducted by any of natural drying, towel drying and drying with a dryer. The hair after shampooing and drying exhibits enhanced lift up and volume-up effect, depression of stiff feel and depression of residue feel.

EXAMPLES

In the following Examples and Comparative Examples, "parts" means "parts by mass" and "%" means "% by mass" as long as it is otherwise specially determined. In addition, the methods for measuring various types of physical properties are as follows.

First of all, a method for producing polymers employed in the following Examples will be described.

Synthesis Example 1

Synthesis of Organo Polysiloxane A 6.5 g (0.042 mol) of diethyl sulfate and 34.4 g (0.36 mol) of 2-ethyl-2-oxazoline were dissolved in 87.0 g of dehydrated ethyl acetate, and then the solution was heated and refluxed for 8 hours within nitrogen atmosphere to synthesize poly(N-propionyl ethyleneimine) having number average molecular weight of $1.3 \times 10^3$. Then, 100 g of side chain-primary aminopropyl-modified poly dimethyl siloxane (weight-average molecular weight: $5 \times 10^4$, amine equivalent: 2,000) was added therein to obtain N-propionyl ethyleneimine-dimethyl siloxane copolymer in a form of light yellow rubber-from semisolid (138 g, yield 98%). The content rate of organo polysiloxane segment in the final product was 71% by mass, and the weight-average molecular weight thereof was $7 \times 10^4$. The results of a neutralization titration with hydrochloric acid employing methanol as a solvent indicated that amino group of about 20% by mass remained in the final product. In addition, the mass ratio (a/b) of organo polysiloxane segment constituting main chain (a) and poly(N-acylalkylene imine) segment (b) was 71/29.

Synthesis Example 2

Synthesis of Organo Polysiloxane B 6.2 g (0.040 mol) of diethyl sulfate and 27.2 g (0.27 mol) of 2-ethyl-2-oxazoline were dissolved in 67.7 g of dehydrated ethyl acetate, and then the solution was heated and refluxed for 8 hours within nitrogen atmosphere to synthesize poly(N-propionyl ethyleneimine) having number average molecular weight of $8 \times 10^2$. Then, 100 g of side chain-primary aminopropyl-modified poly dimethyl siloxane (weight-average molecular weight: $5 \times 10^4$, amine equivalent: 2,000) was added therein to obtain N-propionyl ethyleneimine-dimethyl siloxane copolymer in a form of light yellow rubber-from semisolid (131 g, yield 98%). The content rate of organo polysiloxane segment in the final product was 75% by mass, and the weight-average molecular weight thereof was $6.7 \times 10^4$.

The results of a neutralization titration with hydrochloric acid employing methanol as a solvent indicated that amino group of about 20% by mass remained in the final product. In addition, the mass ratio (a/b) of organo polysiloxane segment constituting main chain (a) and poly(N-acylalkylene imine) segment (b) was 75/25.

Synthesis Example 3

Synthesis of Organo Polysiloxane C 5.5 g (0.036 mol) of diethyl sulfate and 144.5 g (1.46 mol) of 2-ethyl-2-oxazoline were dissolved in 304.6 g of dehydrated ethyl acetate, and then the solution was heated and refluxed for 8 hours within nitrogen atmosphere to synthesize poly(N-propionyl ethyleneimine) having number average molecular weight of $4.3 \times 10^3$. Then, 100 g of side chain-primary aminopropyl-modified poly dimethyl siloxane (weight-average molecular weight: $5 \times 10^4$, amine equivalent: 2,000) was added therein to obtain N-propionyl ethyleneimine-dimethyl siloxane copolymer in a form of light yellow solid (245 g, yield 98%). The content rate of organo polysiloxane segment in the final product was 40% by mass, and the weight-average molecular weight thereof was $1.25 \times 10^5$. The results of a neutralization titration with hydrochloric acid employing methanol as a solvent indicated that amino group of about 29% by mass remained in the final product. In addition, the mass ratio (a/b) of organo polysiloxane segment constituting the main chain (a) and poly(N-acylalkylene imine) segment (b) was 50/50.

Synthesis Example 4

Synthesis of Organo Polysiloxane D 0.8 g (0.005 mol) of diethyl sulfate and 12.8 g (0.14 mol) of 2-ethyl-2-oxazoline were dissolved in 29.0 g of dehydrated ethyl acetate, and then the solution was heated and refluxed for 8 hours within nitrogen atmosphere to obtain poly(N-propionyl ethyleneimine) having number average molecular weight of $2.7 \times 10^3$. Further, 100 g of side chain-primary aminopropyl-modified poly dimethyl siloxane (weight-average molecular weight: $1 \times 10^5$, amine equivalent: 20,000) was added therein to obtain N-propionyl ethyleneimine-dimethyl siloxane copolymer in a form of light yellow rubber-from solid (111 g, yield 98%). The content rate of organo polysiloxane segment in the final product was 88% by mass, and the weight-average molecular weight thereof was $1.1 \times 10^5$. The results of a neutralization titration with hydrochloric acid employing methanol as a solvent indicated that none of amino group remained in the final product. In addition, the mass ratio (a/b) of organo polysiloxane segment constituting the main chain (a) and poly(N-acylalkylene imine) segment (b) was 88/12.

Physical properties of organo polysiloxanes A to D obtained in Synthesis Examples 1 to 4 and other polymers employed in the following examples are shown in Table 1.

TABLE 1

| | STORAGE ELASTIC MODULUS (20° C./Pa) | ADHESIVENESS (20° C./gf) |
|---|---|---|
| POLY(N-ACYLALKYLENE IMINE)-MODIFIED SILICONE OBTAINED IN SYNTHESIS EXAMPLE 1 (ORGANO POLYSILOXANE A) | $2 \times 10^6$ | 193 |
| POLY(N-ACYLALKYLENE IMINE)-MODIFIED SILICONE OBTAINED IN SYNTHESIS EXAMPLE 2 (ORGANO POLYSILOXANE B) | $6 \times 10^5$ | 380 |
| POLY(N-ACYLALKYLENE IMINE)-MODIFIED SILICONE OBTAINED IN SYNTHESIS EXAMPLE 3 (ORGANO POLYSILOXANE C) | $5 \times 10^8$ | 1 |
| POLY(N-ACYLALKYLENE IMINE)-MODIFIED SILICONE OBTAINED IN SYNTHESIS EXAMPLE 4 (ORGANO POLYSILOXANE D) | $3 \times 10^4$ | 6 |
| ALKYL-MODIFIED SILICONE (CLARIANT, SilCare Silicone 41M80) | $3 \times 10^7$ | 3 |
| DIMETHYLAMINOETHYL METHACRYLATE COPOLYMER-TYPE CATIONIC POLYMER (GAF, Gafquat755N) | $1.5 \times 10^9$ | 1 |

In addition to above, the storage elastic modulus and adhesion of the polymer obtained in the respective Synthesis Examples in Table 1 were respectively measured by the above-described method described in the section of the description of Embodiments.

Examples 1 to 9, Comparative Examples 1 to 9

The aqueous hair cleansing agents (shampoo) shown in Table 2 were prepared by an ordinary method, and were evaluated by the following evaluating method. The results are shown in Table 2. In the table, pH is the value of solutions of the respective compositions diluted by 20-mass times with water, measured at 25 degrees C.

(1) Lift Up of Hair (Hair Root)

FIG. 1 is a photo for describing a method for evaluating ease of lift up of the hair in the present Example. A tress (hair: 30 cm-long), in which hair strands were fixed on a sheet having an area of 7×7 cm at an angle of 60 degree in the same direction (for the sheet) at a density of 200 strands/cm$^2$, was employed. The present tress was shampooed and rinsed with the respective test samples (2 g), and then, was dried at 50 degrees C. (with a drier machine) while the tress was oriented downward (so that the hair was hanged down), and then, the surface thereof having the fixed hair strands was turned upward to arrange the entire hair toward the inverse direction to the fixing direction, and the height (height between arrow in FIG. 1) from the sheet to the top (uppermost surface) of the hair was measured.

(2) Voluminous Feel of Appearance After Drying

A wig implanted with Caucasian hair (blond) (head of a mannequin, length of hair was short to medium) was employed, and was shampooed and rinsed with the respective test samples (6 g), and then, was dried with a towel and was completely dried with a drier (finger combing only), and then the voluminous feel of the appearance was determined by 5-scale evaluation. The judgment was made in reference to the voluminous feel obtained with the standard shampoo made with the following formulation as the standard (3 points for the evaluation). It was determined that 5 points of the evaluation was very voluminous; 4 points of the evaluation was voluminous; 2 points of the evaluation was not very voluminous; and 1 point of the evaluation was not voluminous, and the presented score was obtained by the integrated value of six persons (30 points for perfect score).

Formulation of Standard Shampoo (pH 6.3)
polyoxyethylene (2) lauryl ether sodium sulfate salt: 10.6% by mass
sodium lauryl sulfate: 4.0% by mass
sodium chloride: 0.5% by mass
cocamidopropyl betaine: 3.0% by mass
benzyl alcohol: 0.3% by mass
malic acid: 0.1% by mass
pure water: the rest.

In addition, sensory evaluation was conducted while 10 g of bundle of the hair in weight (5 cm wide, 25 cm long) was processed by the following method. It was shampooed with 2 g of the aqueous hair cleansing agent shown in Table 2, and then was rinsed for 30 seconds with running water at about 40 degrees C., and then was dried with a towel and was completely dried with a drier, and then sensory evaluations were conducted by specialty panelists. The shown score was obtained as the integrated value of six persons (30 points for perfect score).

(3) Absence of Coarse Feel of Hair After Drying
5: no coarse feel;
4: not much coarse feel;
3: slightly coarse feel;
2: coarse feel; and
1: very coarse feel.

(4) Absence of Residue Feel (Oily Feel)
5: no residue feel;
4: not much residue feel;
3: slight residue feel;
2: residue feel; and
1: much residue feel.

(5) Smoothness in Rinsing
5: feel very smooth;
4: feel smooth;
3: moderately feel smooth;
2: feel not much smooth; and
1: feel no smoothness.

TABLE 2

| | | EXAMPLES | | | | | | | | | COMPARATIVE EXAMPLES | | | | | | | | |
|---|---|---|---|---|---|---|---|---|---|---|---|---|---|---|---|---|---|---|---|
| | | 1 | 2 | 3 | 4 | 5 | 6 | 7 | 8 | 9 | 1 | 2 | 3 | 4 | 5 | 6 | 7 | 8 | 9 |
| FORMU-LATION (% BY MASS) | (A) SODIUM LAURYL ETHER SULFATE (EO2 MOL)*1 | 10.6 | 10.6 | — | 10.6 | 10.6 | 10.6 | 10.6 | 10.6 | 10.6 | 10.6 | 10.6 | 10.6 | 10.6 | 10.6 | 10.6 | 10.6 | 10.6 | 10.6 |
| | SODIUM LAURYL ETHER SULFATE (EO1 MOL)*2 | — | — | 14.6 | — | — | — | — | — | — | — | — | — | — | — | — | — | — | — |
| | SODIUM LAURYL SULFATE | 4.0 | 4.0 | — | 4.0 | 4.0 | 4.0 | 4.0 | 4.0 | 4.0 | 4.0 | 4.0 | 4.0 | — | 4.0 | 4.0 | 4.0 | 4.0 | 4.0 |
| | (B) POLY(N-ACYL-ALKYLENE IMINE)-MODIFIED SILICONE OBTAINED IN SYNTHESIS EXAMPLE 1 (ORGANO POLYSIL-OXANE A) | 1.0 | 1.0 | 1.0 | — | 1.0 | 0.5 | 2.0 | 1.0 | 1.0 | — | 1.0 | — | — | — | — | — | — | — |
| | POLY(N-ACYL-ALKYLENE IMINE)-MODIFIED SILICONE OBTAINED IN SYNTHESIS EXAMPLE 2 (ORGANO POLYSIL-OXANE B) | — | — | — | 1.0 | — | — | — | — | — | — | — | — | — | — | — | — | — | — |
| OTHER POLYMER COMPO-NENTS | POLY(N-ACYL-ALKYLENE IMINE)-MODIFIED SILICONE OBTAINED IN SYNTHESIS | — | — | — | — | — | — | — | — | — | — | — | 1.0 | — | — | — | 1.0 | 1.0 | — |

TABLE 2-continued

| | EXAMPLES | | | | | | | | | COMPARATIVE EXAMPLES | | | | | | | | |
|---|---|---|---|---|---|---|---|---|---|---|---|---|---|---|---|---|---|---|
| | 1 | 2 | 3 | 4 | 5 | 6 | 7 | 8 | 9 | 1 | 2 | 3 | 4 | 5 | 6 | 7 | 8 | 9 |
| EXAMPLE 3 (ORGANOPOLYSILOXANE C) | — | — | — | — | — | — | — | — | — | — | — | — | — | — | — | — | — | — |
| POLY(N-ACYL-ALKYLENE IMINE)-MODIFIED SILICONE OBTAINED IN SYNTHESIS EXAMPLE 4 (ORGANOPOLYSILOXANE D) | — | — | — | — | — | — | — | — | — | — | — | — | 1.0 | — | — | — | — | — |
| ALKYL-MODIFIED SILICONE (CLARIANT, SilCare Silicone 41M80) | — | — | — | — | — | — | — | — | — | — | — | — | — | 1.0 | 1.0 | — | — | — |
| DIMETHYL-AMINOETHYL METHACRYLATE COPOLYMER-TYPE CATIONIC POLYMER (GAF, Gafquat755N) | — | — | — | — | — | — | — | — | — | — | — | — | — | — | — | 0.2 | — | — |
| (C) CATIONIZED GUAR GUM*3 | 0.2 | 0.2 | 0.2 | 0.2 | — | 0.5 | 0.1 | — | — | 0.2 | — | 0.2 | 0.2 | 0.2 | 0.2 | — | — | — |
| CATIONIZED LOCUST BEAN GUM*4 | — | — | — | — | 0.2 | — | — | — | — | — | — | — | — | — | — | — | — | — |
| CATIONIZED HYDROXYETHYL CELLULOSE*5 | — | — | — | — | — | — | — | 0.2 | — | — | — | — | — | — | — | — | — | — |
| DIMETHYL-DIALLYL-AMMONIUM CHLORIDE-ACRYLAMIDE COPOLYMER*6 | — | — | — | — | — | — | — | — | 0.2 | — | — | — | — | — | — | — | — | — |
| OTHER COMPO- HYDROXYETHYL | — | — | — | — | — | — | — | — | — | — | — | — | — | — | — | — | 0.2 | — |

TABLE 2-continued

| | | EXAMPLES | | | | | | | | | COMPARATIVE EXAMPLES | | | | | | | | |
|---|---|---|---|---|---|---|---|---|---|---|---|---|---|---|---|---|---|---|---|
| | | 1 | 2 | 3 | 4 | 5 | 6 | 7 | 8 | 9 | 1 | 2 | 3 | 4 | 5 | 6 | 7 | 8 | 9 |
| NENTS | CELLULOSE*7 | — | — | — | — | — | — | — | — | — | — | — | — | — | — | — | — | — | — |
| | POLYVINYL ALCOHOL*8 | — | — | — | — | — | — | — | — | — | — | — | — | — | — | — | — | — | 0.2 |
| | SODIUM CHLORIDE | — | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 |
| | COCAMIDO-PROPYL BETAINE | 3.0 | 3.0 | 3.0 | 3.0 | 3.0 | 3.0 | 3.0 | 3.0 | 3.0 | 3.0 | 3.0 | 3.0 | 3.0 | 3.0 | 3.0 | 3.0 | 3.0 | 3.0 |
| | BENZYL ALCOHOL | 0.3 | 0.3 | 0.3 | 0.3 | 0.3 | 0.3 | 0.3 | 0.3 | 0.3 | 0.3 | 0.3 | 0.3 | 0.3 | 0.3 | 0.3 | 0.3 | 0.3 | 0.3 |
| | MALIC ACID | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| | PURE WATER | BAL-ANCE | BAL-ANCE | BAL-ANCE | BAL-ANCE | BAL-ANCE | BAL-ANCE | BAL-ANCE | BAL-ANCE | BAL-ANCE | BAL-ANCE | BAL-ANCE | BAL-ANCE | BAL-ANCE | BAL-ANCE | BAL-ANCE | BAL-ANCE | BAL-ANCE | BAL-ANCE |
| pH | | 6.1 | 6.3 | 6.1 | 6.0 | 6.1 | 5.9 | 6.4 | 6.1 | 6.4 | 6.2 | 6.1 | 6.0 | 6.1 | 6.2 | 6.3 | 6.0 | 5.9 | 5.9 |
| (B)/(C) MASS RATIO | | 5 | 5 | 5 | 5 | 5 | 1 | 20 | 5 | 5 | — | — | — | — | — | — | — | — | — |
| EVALU-ATION RESULTS | EASE OF LIFT-UP OF THE HAIR (mm) | 27 | 29 | 30 | 33 | 27 | 28 | 30 | 25 | 26 | 23 | 25 | 23 | 21 | 25 | 23 | 24 | 24 | 25 |
| | VOLUMINOUS FEEL AFTER DRYING | 24 | 28 | 27 | 29 | 24 | 27 | 23 | 21 | 23 | 12 | 21 | 12 | 12 | 18 | 21 | 20 | 21 | 20 |
| | ABSENCE OF RESIDUE FEEL AFTER DRYING | 27 | 25 | 24 | 24 | 26 | 26 | 23 | 28 | 24 | 28 | 25 | 27 | 13 | 18 | 29 | 23 | 24 | 26 |
| | ABSENCE OF COARSE FEEL AFTER DRYING | 24 | 24 | 28 | 23 | 23 | 23 | 27 | 17 | 25 | 10 | 18 | 12 | 27 | 27 | 11 | 19 | 22 | 20 |
| | SMOOTHNESS IN RINSING | 26 | 28 | 28 | 24 | 25 | 26 | 24 | 26 | 25 | 28 | 23 | 27 | 13 | 18 | 15 | 18 | 15 | 13 |

*1sodium lauryl ether sulfate (EO 2 mol); sodium polyoxyethylene (2) lauryl ether sulfate, mass average addition molar number of ethylene oxide is 2;
*2sodium lauryl ether sulfate (EO 1 mol); sodium polyoxyethylene (1) lauryl ether sulfate, mass average addition molar number of ethylene oxide is 1;
*3cationized guar gum: Jaguar C-17 (commercially available from Rhodia);
*4cationized locust bean gum: Catinal CLB-100 (commercially available from Toho Chemical Industry Co., Ltd.);
*5cationized hydroxyethyl cellulose: Caticelo M-80 (commercially available from Kao Co., Ltd.);
*6dimethyl diallyl ammonium chloride-acrylamide copolymer: Merquat 550 (commercially available from The Lubrizol Corporation);
*7hydroxyethyl cellulose: HEC4400h (commercially available from Sumitomo Seika Chemicals Co., Ltd.); and
*8polyvinyl alcohol: Polyvinyl alcohol (Nippon Synthetic Chemical Industry).

Examples 10-11

The aqueous hair cleansing agents shown below were prepared by an ordinary method, and were evaluated. Here, pH is the value of solutions of the respective compositions diluted by 20-mass times with water, measured at 25 degrees C.

Example 10

Shampoo (pH 6.0)

sodium lauryl ether (2) sulfate: 10.6% by mass;
sodium lauryl sulfate: 4.0% by mass;
poly(N-acylalkylene imine)-modified silicone obtained in Synthesis Example 2 (organo polysiloxane B): 0.5% by mass;
cationized guar gum (commercially available from Rhodia: Jaguar C-14S): 0.2% by mass;
sodium chloride: 0.5% by mass;
cationized hydroxyethyl cellulose (commercially available from Kao Co., Ltd.: Poiz M-80): 0.1% by mass;
dimethyl diallyl ammonium chloride-acrylamide copolymer solution (commercially available from Lubrizol Corporation: Merquat 550): 0.2% by mass;
lauric acid: 0.4% by mass;
cocamidopropyl betaine: 3.0% by mass;
isodecyl glyceryl ether: 0.5% by mass;
ethylene glycol distearyl: 1.5% by mass;
myristyl alcohol: 0.3% by mass;
dimethyl polysiloxane: 0.5% by mass;
polypropylene(7)glycol (molecular weight 420): 0.1% by mass;
dipotassium glycyrrhizate: 0.1% by mass;
zinc pyrithione: 1.0% by mass;
benzyl alcohol: 0.3% by mass;
malic acid (50% solution): 0.1% by mass;
lactic acid (90% solution): 0.1% by mass;
sodium benzoate: 0.1% by mass;
ethanol: 0.3% by mass;
eucalyptus extract: 0.1% by mass;
chamomilla extract: 0.05% by mass;
panthenol: 0.05% by mass;
silk extract: 0.05% by mass;
aloe extract: 0.05% by mass;
seaweed extract: 0.05% by mass;
orange oil: 0.05% by mass;
potassium hydroxide: proper amount;
perfume: proper amount; and
pure water: the rest.

The shampoo of Example 10 exhibited enhanced lift-up and volume-up effect of the hair after shampooing and drying, and the coarse feel and the residue feel were reduced.

Example 11

Shampoo (pH 5.8)

sodium lauryl ether (2) sulfate: 10.6% by mass;
sodium lauryl sulfate: 4.0% by mass;
poly(N-acylalkylene imine)-modified silicone obtained in Synthesis Example 2 (organo polysiloxane B): 0.5% by mass;
cationized guar gum (commercially available from Rhodia: Jaguar C-14S): 0.2% by mass;
sodium chloride: 0.5% by mass;
cationized hydroxyethyl cellulose (commercially available from Kao Co., Ltd.: Poiz M-80): 0.1% by mass;
dimethyl diallyl ammonium chloride-acrylamide copolymer solution (commercially available from Lubrizol Corporation: Merquat 550): 0.2% by mass;
lauric acid: 0.4% by mass;
cocamidopropyl betaine: 3.0% by mass;
isodecyl glyceryl ether: 0.5% by mass;
ethylene glycol distearyl: 1.5% by mass;
myristyl alcohol: 0.3% by mass;
dimethyl polysiloxane: 0.5% by mass;
polypropylene(7)glycol (molecular weight 420): 0.1% by mass;
dipotassium glycyrrhizate: 0.1% by mass;
piroctone olamine: 0.5% by mass (commercially available from Rhodia: Octopirox);
benzyl alcohol: 0.3% by mass;
malic acid (50% solution): 0.1% by mass;
lactic acid (90% solution): 0.1% by mass;
sodium benzoate: 0.1% by mass;
ethanol: 0.3% by mass;
eucalyptus extract: 0.1% by mass;
chamomilla extract: 0.05% by mass;
panthenol: 0.05% by mass;
silk extract: 0.05% by mass;
aloe extract: 0.05% by mass;
seaweed extract: 0.05% by mass;
orange oil: 0.05% by mass;
potassium hydroxide: proper amount;
perfume: proper amount; and
pure water: the rest.

The shampoo of Example 11 exhibited enhanced rising and volume-up effect of the hair after shampooing and drying, and the coarse feel and the residue feel were reduced.

The present invention also includes the following embodiments.

<1>

An aqueous hair cleansing agent containing the following components (A), (B) and (C) and water:
(A) an anionic surfactant;
(B) an organo polysiloxane, in which a poly(N-acyl alkylene imine) segment composed of repeating units represented by the following general formula (1) is bound to at least two silicon atoms in organo polysiloxane segment constituting a main chain through alkylene group containing hetero atom,

(1)

wherein, in the above-described general formula (1), $R^6$ represents a hydrogen atom, or alkyl group, aralkyl group or aryl group of 1 to 22 carbon atom(s), and n represents 2 or 3, wherein number average molecular weight of the poly (N-acyl alkylene imine) segment is within a range from $5.0 \times 10^2$ to $1.8 \times 10^3$, mass ratio (a/b) of the organo polysiloxane segment (a) constituting the main chain and the poly(N-acyl alkylene imine) segment (b) is within a range from 65/35 to 82/18, and weight-average molecular weight of the organo polysiloxane segment constituting the main chain is within a range from $1 \times 10^4$ to $1 \times 10^5$; and (C) one or more of cationized polymer(s) selected from (c-1) and (c-2):
(c-1) a cationized polymer having cellulose skeleton or galactomannan skeleton; and
(c-2) a cationic polymer having diallyl dimethylammonium salt skeleton.
<2>
An aqueous hair cleansing agent containing the following components (A), (B) and (C) and water:
(A) an anionic surfactant;
(B) an organo polysiloxane, in which a poly(N-acyl alkylene imine) segment composed of repeating units represented by the following general formula (1) is bound to at least two silicon atoms in organo polysiloxane segment constituting the main chain through alkylene group containing hetero atom,

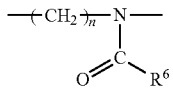

(1)

wherein, in the above-described general formula (1), $R^6$ represents a hydrogen atom, or alkyl group, aralkyl group or aryl group of 1 to 22 carbon atom(s), and n represents 2 or 3, wherein number average molecular weight of the poly (N-acyl alkylene imine) segment is within a range from $5.0 \times 10^2$ to $1.8 \times 10^3$, mass ratio (a/b) of the organo polysiloxane segment (a) constituting the main chain and the poly(N-acyl alkylene imine) segment (b) is within a range from 65/35 to 82/18, and weight-average molecular weight of the organo polysiloxane segment constituting the main chain is within a range from $1 \times 10^4$ to $1 \times 10^5$; and
(C) cationized galactomannan having ratio of galactose and mannose of 1:2 to 1:4.
<3>
An aqueous hair cleansing agent containing the following components (A), (B) and (C) and water:
(A) an anionic surfactant;
(B) a polymer, in which storage elastic modulus at 20 degrees C. is within a range from $1 \times 10^5$ to $1 \times 10^7$ Pa, which is measured under the condition that the temperature is elevated at a speed of 5 degrees C./2 minutes after the temperature is decreased from 25 degrees C. to −130 degrees C. in 30 minutes at a frequency of 2 Hz and with a strain of 0.01%; adhesion measured according to JIS-Z 3284 is within a range from 50 to 500 gf; and weight-average molecular weight thereof is within a range from $5 \times 10^2$ to $5 \times 10^5$; and
(C) cationized galactomannan having ratio of galactose and mannose of 1:2 to 1:4.
<4>
The aqueous hair cleansing agent according to the above-described <3>, wherein the above-described component (B) is configured that a poly(N-acyl alkylene imine) segment composed of repeating units represented by the following general formula (1) is bound to at least two silicon atoms in organo polysiloxane segment constituting main chain through alkylene group containing hetero atom,

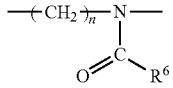

(1)

wherein, in the above-described general formula (1), $R^6$ represents a hydrogen atom, or alkyl group, aralkyl group or aryl group of 1 to 22 carbon atom(s), and n represents 2 or 3,
wherein number average molecular weight of the poly (N-acyl alkylene imine) segment is within a range from $5.0 \times 10^2$ to $1.8 \times 10^3$, mass ratio (a/b) of the organo polysiloxane segment (a) constituting the main chain and the poly(N-acyl alkylene imine) segment (b) is within a range from 65/35 to 82/18, and weight-average molecular weight of the organo polysiloxane segment constituting the main chain is within a range from $1 \times 10^4$ to $1 \times 10^5$.
<5>
The aqueous hair cleansing agent according to any one of the above-described <1>, <2> and <4>, wherein number average molecular weight of the poly (N-acylalkylene imine) segment is equal to or higher than $8.0 \times 10^2$ and equal to or lower than $1.4 \times 10^3$.
<6>
The aqueous hair cleansing agent according to any one of the above-described <1>, <2>, <4> and <5>, wherein mass ratio (a/b) of the organo polysiloxane segment (a) constituting the main chain and the poly(N-acyl alkylene imine) segment (b) is within a range from 70/30 to 79/21.
<7>
The aqueous hair cleansing agent according to any one of the above-described <1>, <2> and <4> to <6>, wherein weight-average molecular weight of the organo polysiloxane segment constituting the main chain is equal to or higher than $1.7 \times 10^3$ and equal to or lower than $3.0 \times 10^3$.
<8>
The aqueous hair cleansing agent according to any one of the above-described <1> to <7>, wherein the component (B) is a polymer, in which storage elastic modulus at 20 degrees C. is within a range from $1 \times 10^5$ to $1 \times 10^7$ Pa, which is measured under the condition that the temperature is elevated at a speed of 5 degrees C./2 minutes after the temperature is decreased from 25 degrees C. to −130 degrees C. in 30 minutes at a frequency of 2 Hz and with a strain of 0.01%, and is preferably within a range from $3 \times 10^5$ to $8 \times 10^6$ Pa, and is further preferably within a range from $5 \times 10^4$ to $1 \times 10^6$ Pa, or in which storage elastic modulus at 80 degrees C. is within a range from $3 \times 10^4$ to $1 \times 10^5$ Pa, which is measured under the condition that the temperature is elevated at a speed of 5 degrees C./2 minutes after the temperature is decreased from 25 degrees C. to −130 degrees C. in 30 minutes at a frequency of 2 Hz and with a strain of 0.01%, adhesion measured according to JIS-Z 3284 is within a range from 50 to 500 gf, and is preferably a range from 100 to 400 gf, and weight-average molecular weight thereof is within a range from $5 \times 10^2$ to $5 \times 10^5$; and is preferably within a range from $1 \times 10^3$ to $1 \times 10^5$.
<9>
The aqueous hair cleansing agent according to any one of the above-described <1> to <8>, wherein in the whole aqueous hair cleansing agent, content of the component (A) is equal to or higher than 1% by mass and equal to or lower than 30% by mass, content of the component (B) is equal to or higher than 0.05% by mass and equal to or lower than 4% by mass, and content of the component (C) is equal to or higher than 0.01% by mass and equal to or lower than 3% by mass.
<10>
The aqueous hair cleansing agent according to any one of the above-described <1> to <9>, wherein mass ratio (B)/(C) of the component (B) over the component (C) is equal to or higher than 0.2 and equal to or lower than 15.

<11>
The aqueous hair cleansing agent according to any one of the above-described <1> to <10>, wherein mass ratio (B)/(C) of the component (B) over the component (C) is equal to or higher than 0.5 and equal to or lower than 10.
<12>
The aqueous hair cleansing agent according to any one of the above-described <1> to <11>, wherein the component (C) is (c-1).
<13>
The aqueous hair cleansing agent according to the above-described <12>, wherein the (c-1) is one or more selected from cationized cellulose, cationized hydroxyethyl cellulose and cationized guar gum.
<14>
The aqueous hair cleansing agent according to any one of the above-described <1> to <11>, wherein the component (C) is (c-2).
<15>
The aqueous hair cleansing agent according to the above-described <14>, wherein the (c-2) is a binary or ternary cationized polymer, composed of copolymerization of monomers composing (meta)acrylic acid or (meta)acrylamide.
<16>
The aqueous hair cleansing agent according to any one of the above-described <1> to <11>, wherein the component (C) is cationized galactomannan having ratio of galactose and mannose of 1:2 to 1:4.
<17>
The aqueous hair cleansing agent according to any one of the above-described <1> to <11>, wherein the component (C) is any one of cationized guar gum, cationized locust bean gum, cationized hydroxyethyl cellulose and dimethyl diallyl ammonium chloride-acrylamide copolymer.
<18>
The aqueous hair cleansing agent according to any one of the above-described <1> to <17>, wherein the component (A) is one or more of polyoxyethylene alkyl ether sulfate represented by the following general formula (11):

$$R^{11}O(CH_2CH_2O)_uSO_3M \quad (11)$$

wherein, in the above-described general formula (11), $R^{11}$ represents alkyl group or alkenyl group of 10 to 18 carbon atoms, M represents alkali metal, alkaline earth metal, ammonium, alkanolamine or basic amino acid, and U represents a number of 0.5 to 5 in mass average.
<19>
The aqueous hair cleansing agent according to any one of the above-described <1> to <18>, wherein inorganic salt is contained as salts, and content of the salts in the whole aqueous hair cleansing agent is within a range from 0.01 to 2% by mass.
<20>
The aqueous hair cleansing agent according to any one of the above-described <1> to <19>, wherein one or more alcohol(s) selected from group consisting of benzyl alcohol and polypropylene glycol is further contained, and content of the alcohol in the whole aqueous hair cleansing agent is equal to or higher than 0.01% by mass and equal to or lower than 5% by mass.
<21>
The aqueous hair cleansing agent according to any one of the above-described <1> to <20>, wherein an organic acid of 2 to 8 carbon atoms is further contained, and content of the organic acid in the whole aqueous hair cleansing agent is equal to or higher than 0.01% by mass and equal to or lower than 5% by mass.
<22>
Use of the aqueous hair cleansing agent according to the above-described <1> to <21>, for applying over scalp and then foaming, rinsing and drying.

The invention claimed is:
1. A process for providing highly voluminous feel by applying over scalp an aqueous hair cleansing agent and then foaming, rinsing and drying, wherein said aqueous hair cleansing agent comprises components (A), (B), (C) and water:
(A) from 1 to 30% by mass of an anionic surfactant wherein said anionic surfactant is a sulfate-type anionic surfactant or a carboxylic acid-type anionic surfactant;
(B) from 0.05 to 4% by mass of an organo polysiloxane, in which a poly(N-acyl alkylene imine) segment composed of repeating units represented by the following general formula (1) is bound to at least two silicon atoms in an organo polysiloxane segment constituting a main chain through alkylene group comprising a hetero atom,

wherein, in the above-described general formula (1), $R^6$ represents a hydrogen atom, or alkyl group, aralkyl group or aryl group of 1 to 22 carbon atom(s), and n represents 2 or 3,
wherein the number-average molecular weight of the poly (N-acyl alkylene imine) segment is within a range from $5.0 \times 10^2$ to $1.8 \times 10^3$, the mass ratio (a/b) of the organo polysiloxane segment (a) constituting the main chain to the poly(N-acyl alkylene imine) segment (b) is within a range from 65/35 to 82/18, and the weight-average molecular weight of the organo polysiloxane segment constituting the main chain is within a range from $1 \times 10^4$ to $1 \times 10^5$; and
(C) from 0.01 to 3% by mass of one or more cationized polymer(s) selected from the group consisting of (c-1) and (c-2):
(c-1) a cationized polymer having cellulose skeleton or galactomannan skeleton; and
(c-2) a cationic polymer having diallyl dimethylammonium salt skeleton,
wherein the mass ratio (B)/(C) is 0.2 to 20.
2. The process of claim 1, wherein, the content of the component (A) is within a range from 5 to 25% by mass, the content of the component (B) is within a range from 0.1 to 3% by mass, and content of the component (C) is within a range from 0.05 to 2% by mass.
3. The process claim 1, wherein the mass ratio (B)/(C) is 0.5 to 15.
4. The process of claim 1, wherein the component (C) is one or more cationized polymer having cellulose skeleton or galactomannan skeleton.
5. The process of claim 1, wherein component (C) is one or more selected from the group consisting of cationized galactomannan having a ratio of galactose to mannose of 1:2 to 1:4.

6. The process of claim 1, wherein the component (C) is cationized guar gum.

7. The process of claim 1, wherein said aqueous hair cleansing agent further comprises one or more alcohol selected from the group consisting of benzyl alcohol and polypropylene glycol, wherein the content of the alcohol in the whole aqueous hair cleansing agent is within the range of 0.01 to 5% by mass.

8. The process of claim 1, wherein the component (C) is one or more selected from the group consisting of:
  guar gum having a ratio of galactose to mannose of 1:2;
  tara gum having a ratio of galactose to mannose of 1:3; and
  locust bean gum having a ratio of galactose to mannose of 1:4.

9. The process of claim 1, wherein the component (C) comprises a cationic polymer having moieties of a diallyl dimethylammonium salt and at least one of (meth)acrylic acid and (meth)acrylamide.

10. The process of claim 1, wherein the mass ratio (B)/(C) is 0.2 to 15.

11. The process of claim 1, wherein the mass ratio (B)/(C) is 0.2 to 5.

12. The process of claim 1, wherein said aqueous hair cleansing agent further comprises one or more inorganic salt selected from the group consisting of sodium chloride, sodium sulfate, sodium phosphate, potassium chloride, potassium sulfate and potassium phosphate.

13. The process of claim 1, wherein component (B) comprises at least one of
  an organo polysiloxane having a number-average molecular weight of the poly (N-acyl alkylene imine) segment $1.3 \times 10^3$, the mass ratio (a/b) of the organo polysiloxane segment (a) constituting the main chain to the poly(N-acyl alkylene imine) segment (b) is 71/29, and a weight-average molecular weight of the organo polysiloxane segment constituting the main chain is $7 \times 10^4$; and
  an organo polysiloxane having a number-average molecular weight of the poly (N-acyl alkylene imine) segment $8 \times 10^2$, the mass ratio (a/b) of the organo polysiloxane segment (a) constituting the main chain to the poly(N-acyl alkylene imine) segment (b) is 75/25, and a weight-average molecular weight of the organo polysiloxane segment constituting the main chain is $6.7 \times 10^4$, and component (C) comprises at least one of cationized guar gum; cationized locust bean gum; and cationized hydroxyethyl cellulose.

14. The process of claim 1, wherein said anionic surfactant is a sulfate-type anionic surfactant.

15. The process of claim 1, wherein said sulfate-type anionic surfactant is selected from the group consisting of an alkyl sulfate, an alkenyl sulfate, a polyoxyalkylene alkyl ether sulfate, a polyoxyalkylene alkenyl ether sulfate, and an alkylene sulfosuccinate alkyl phenyl ether sulfate.

16. The process of claim 1, wherein said anionic surfactant is a carboxylic acid-type anionic surfactant.

17. The process of claim 1, wherein said carboxylic acid-type anionic surfactant is selected from the group consisting of a higher fatty acid salt, an alkyl ether carboxylic acid, and a salt of an alkyl ether carboxylic acid.

* * * * *